(12) United States Patent
Beaucage et al.

(10) Patent No.: US 7,355,037 B2
(45) Date of Patent: Apr. 8, 2008

(54) THERMOLABILE HYDROXYL PROTECTING GROUPS AND METHODS OF USE

(75) Inventors: Serge L. Beaucage, Silver Spring, MD (US); Andrzej Grajkowski, Bethesda, MD (US); Andrzej Wilk, N. Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 497 days.

(21) Appl. No.: 10/497,416

(22) PCT Filed: Dec. 3, 2002

(86) PCT No.: PCT/US02/38400

§ 371 (c)(1),
(2), (4) Date: Aug. 16, 2004

(87) PCT Pub. No.: WO03/048179

PCT Pub. Date: Jun. 12, 2003

(65) Prior Publication Data

US 2005/0020827 A1 Jan. 27, 2005

Related U.S. Application Data

(60) Provisional application No. 60/336,745, filed on Dec. 3, 2001.

(51) Int. Cl.
*C07H 21/00* (2006.01)

(52) U.S. Cl. .............................. 536/25.31; 536/25.33; 536/25.34

(58) Field of Classification Search ............ 536/25.31, 536/25.33, 25.34
See application file for complete search history.

(56) References Cited

U.S. PATENT DOCUMENTS 3,534,017 A 10/1970 Fujimoto et al.

(Continued)

FOREIGN PATENT DOCUMENTS

EP 0 006 220 A1 1/1980

(Continued)

OTHER PUBLICATIONS

Chmielewski et al., "Thermolytic Carbonates for Potential 5'-Hydroxyl Protection of Deoxyribonucleosides," □□J. Organic Chemistry, 68(26), 10003-10012 (2003): WEB Pub. on Nov. 25, 2003.*

(Continued)

*Primary Examiner*—L. E. Crane
(74) *Attorney, Agent, or Firm*—Leydig, Voit & Mayer, Ltd.

(57) ABSTRACT

Provided is a hydroxyl-protected alcohol of the formula R—O—Pg, wherein Pg is a protecting group of the formula:

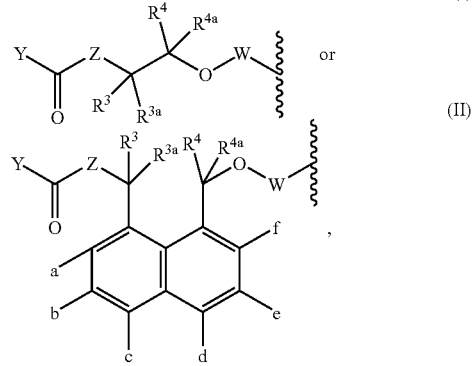

wherein Y, Z, W, $R^1$, $R^{1a}$, $R^2$, $R^{2a}$, $R^3$, $R^{3a}$, $R^4$, $R^{4a}$, a, b, c, d, e and f are defined herein and R is a nucleosidyl group, an oligonucleotidyl group with 2 to about 300 nucleosides, or an oligomer with 2 to about 300 nucleosides. Also provided is a deprotection method, which includes heating the hydroxyl-protected alcohol at a temperature effective to cleave thermally the hydroxyl-protecting group therefrom.

26 Claims, 5 Drawing Sheets

| | | |
|---|---|---|
| 4,415,732 A | 11/1983 | Caruthers et al. |
| 4,417,046 A | 11/1983 | Hsiung |
| 4,458,066 A | 7/1984 | Caruthers et al. |
| 4,663,446 A | 5/1987 | Wright |
| 4,668,777 A | 5/1987 | Caruthers et al. |
| 4,725,677 A | 2/1988 | Köster et al. |
| 4,739,044 A | 4/1988 | Stabinsky |
| 4,757,141 A | 7/1988 | Fung et al. |
| 4,808,708 A | 2/1989 | Yoshida et al. |
| 4,816,569 A | 3/1989 | Miyoshi |
| 4,816,570 A | 3/1989 | Farquhar |
| 4,845,205 A | 7/1989 | Dinh et al. |
| 4,849,513 A | 7/1989 | Smith et al. |
| 4,950,745 A | 8/1990 | Ishido et al. |
| 4,973,679 A | 11/1990 | Caruthers et al. |
| 4,980,460 A | 12/1990 | Molko et al. |
| 5,026,838 A | 6/1991 | Nojiri et al. |
| 5,039,796 A | 8/1991 | Engels et al. |
| 5,071,974 A | 12/1991 | Groody |
| 5,091,519 A | 2/1992 | Cruickshank |
| 5,134,228 A | 7/1992 | Takaku |
| RE34,069 E | 9/1992 | Köster et al. |
| 5,166,330 A | 11/1992 | Engels et al. |
| 5,212,304 A | 5/1993 | Fung et al. |
| 5,214,135 A | 5/1993 | Srivastava et al. |
| 5,252,760 A | 10/1993 | Urdea et al. |
| 5,258,538 A | 11/1993 | Fung et al. |
| 5,324,831 A | 6/1994 | Marquez et al. |
| 5,332,845 A | 7/1994 | Ureda et al. |
| 5,348,868 A | 9/1994 | Reddy et al. |
| 5,428,148 A | 6/1995 | Reddy et al. |
| 5,430,138 A | 7/1995 | Urdea et al. |
| 5,449,602 A | 9/1995 | Royer et al. |
| 5,506,351 A | 4/1996 | McGee |
| 5,510,476 A | 4/1996 | Ravikumar et al. |
| 5,518,651 A | 5/1996 | Reddy et al. |
| 5,519,126 A | 5/1996 | Hecht |
| 5,525,719 A | 6/1996 | Srivastava et al. |
| 5,556,961 A | 9/1996 | Foote et al. |
| 5,571,902 A | 11/1996 | Ravikumar et al. |
| 5,574,146 A | 11/1996 | Reddy et al. |
| 5,614,622 A | 3/1997 | Iyer et al. |
| 5,616,700 A | 4/1997 | Reddy et al. |
| 5,623,068 A | 4/1997 | Reddy et al. |
| 5,639,867 A | 6/1997 | Brill |
| 5,645,985 A | 7/1997 | Froehler et al. |
| 5,646,265 A | 7/1997 | McGee |
| 5,652,358 A | 7/1997 | Pfleiderer et al. |
| 5,670,489 A | 9/1997 | Baxter et al. |
| 5,681,940 A | 10/1997 | Wang et al. |
| 5,700,919 A | 12/1997 | Seliger et al. |
| 5,703,218 A | 12/1997 | Urdea et al. |
| 5,703,223 A | 12/1997 | Wickstrom et al. |
| 5,705,621 A | 1/1998 | Ravikumar |
| 5,712,378 A | 1/1998 | Wang |
| 5,714,597 A | 2/1998 | Ravikumar et al. |
| 5,731,429 A | 3/1998 | Reddy et al. |
| 5,763,599 A | 6/1998 | Pfleiderer et al. |
| 5,866,700 A | 2/1999 | Pfleiderer et al. |
| 5,889,165 A | 3/1999 | Fodor et al. |
| 5,908,926 A | 6/1999 | Pirrung et al. |
| 5,959,099 A | 9/1999 | Cheruvallath et al. |
| 6,001,982 A | 12/1999 | Ravikumar et al. |
| 6,022,963 A | 2/2000 | McGall et al. |
| 6,043,060 A | 3/2000 | Imanishi |
| 6,762,298 B2 * | 7/2004 | Beaucage et al. ........ 536/25.31 |
| 2001/0044529 A1 | 11/2001 | Beaucage et al. |
| 2005/0020827 A1 * | 1/2005 | Beaucage et al. ............ 536/53 |

FOREIGN PATENT DOCUMENTS

| | | |
|---|---|---|
| EP | 0 090 789 A1 | 10/1983 |
| EP | 0 196 101 A2 | 10/1986 |
| EP | 0 219 342 A2 | 4/1987 |
| EP | 0 241 363 A1 | 10/1987 |
| EP | 0 323 152 A2 | 7/1989 |
| GB | 2 153 356 | 8/1985 |
| WO | WO 88/02004 A1 | 3/1988 |
| WO | WO 93/12132 A1 | 6/1993 |
| WO | WO 00/56749 A1 | 9/2000 |

OTHER PUBLICATIONS

Grajkowski et al. (I), "Conceptual "Heat-Driven" Approach to the Synthesis of DNA Oligonucleotides on Microarrays," Annals N. Y. Academy Sciences, 1002, 1-11 (2003).*
Grajkowski et al. (II), "The 2-(N-Formyl-N-methyl)aminoethyl Group as a Potential Phosphate/ Thiophosphate Protecting Group in Solid-Phase Oligodeoxyribonucleotide Synthesis," Organic Letters. 3(9), 1287-1290 (2001); WEB publ. on Apr. 5, 2001.*
Barone et al., *Nucl. Acids Res.*, 12(10), 4051-4061 (1984).
Beaucage et al., *Ann. New York Acad. Sci.*, 616, 483-485 (1990).
Beaucage et al., *Current Protocols in Nucleic Acid Chemistry*, vol. 1 (Beaucage S.L., Bergstrom, D.E., Glick, G.D., Jones, R.A. eds), John Wiley and Sons: New York (2000) pp. 3.3.1-3.3.20.
Beaucage et al., *Tetrahedron*, 48(12), 2223-2311 (1992).
Beaucage et al., *Tetrahedron*, 49(28), 6123-6194 (1993).
Beaucage, *Methods in Molecular Biology*, vol. 20: Protocols for Oligonucleotides and Analogs, (S. Agrawal, ed.), Humana Press: Totowa, NJ (1993) pp. 33-61.
Bigg et al., *Synthesis*, 277-278 (Mar. 1992).
Boal et al., *Nucl. Acids Res.*, 24(15), 3115-3117 (1996).
Brown et al., *J. Chem. Soc. Chem. Commun.*, 891-893 (1989).
Cao et al., *Tetrahedron Letters*, 24(10), 1019-1020 (1983).
Finger et al., *J. Am. Chem. Soc.*, 81 (10), 2674-2675 (Jun. 2, 1959).
Gardrat et al., *J. Heterocyclic Chem.*, 27, 811-812 (1990).
Grajkowski et al., *Organic Letters*, 3(9), 1287-1290 (2001).
Gray et al., *J. Am. Chem. Soc.*, 81, 4351-4355 (1959).
Guzaev et al., *Tetrahedron Letters*, 41, 5623-5626 (2000).
Iyer et al., *J. Org. Chem.*, 55(15), 4693-4699 (1990).
Iyer et al., *J. Org. Chem.*, 60, 5388-5389 (1995).
Iyer et al., *Tetrahedron: Asymmetry*, 6 (5), 1051-1054 (1995).
Iyer, *Current Protocols in Nucleic Acid Chemistry*, vol. 1 (Beaucage S.L., Bergstrom, D.E., Glick, G.D. Jones R.A. eds); John Wiley and Sons: New York, (2000) pp. 2.1.1-2.1.17.
Kawanobe et al., *Chemistry Letters, Chem. Soc. of Japan*, 825-828 (1982).
Lefebvre et al., *J. Med. Chem.*, 38(2), 3941-3950 (1995).
Martin, *Helv. Chim. Acta.*, 78, 486-504 (1995).
McBride et al., *J. Am. Chem. Soc.*, 108, 2040-2048 (1986).
Mizrakh et al., *Zh. Obs. Khim.*, 45 (10), 2343-2344 (Oct. 1975).
Mizrakh et al., *Zh. Obs. Khim.*, 45 (3), 549-552 (Mar. 1975).
Mizrakh et al., *Zh. Obs. Khim.*, 45 (7), 1469-1473 (Jul. 1975).
Murphy et al., *Tetrahedron*, 47(24), 4077-4088 (1991).
Prakash et al., *Org. Lett.*, 2(25), 3995-3998 (2000).
Probst et al., *Makromol. Chem.*, 177, 2681-2695 (1976).
Pudovik et al., *Chemical Abstracts*, 79(11), 441 (1973).
Pudovik et al., *Chemical Abstracts*, 81(11), 484 (1974).
Regan et al., *Org. Prep. Proc. Int.*, 24(4), 488-492 (1992).
Saegusa et al., *Makromol. Chem.*, 177, 2271-2283 (1976).
Scremin et al., *J. Org. Chem.*, 59 (8), 1963-1966 (1994).

Shibanuma et al., *Chem. Pharm Bull.*, 28(9), 2609-2613 (1980).
Smith et al., *Nucleosides & Nucleotides*, 15(10), 1581-1594 (1996).
Somei et al., *Chem. Pharm. Bull.*, 28 (8), 2515-2518 (1980).
Stec et al., *Nucleic Acids Res.*, 19 (21), 5883-5888 (1991).
Tsuruoka et al., *Tetrahedron Letters*, 40, 8411-8414 (1999).
Waldner et al., *Bioorg. Med. Chem. Letters*, 6(19), 9, 2363-2366 (1996).
Wang et al., *Tetrahedron Letters*, 38(22), 3797-3800 (1997).
Weiner et al., *J. Org. Chem.*, 14, 868-872, (1949).
Wilk et al., *J. Org. Chem.*, 62(20), 6712-6713 (1997).
Wilk et al., *J. Org. Chem.*, 64(20), 7515-7522 (1999).
Wilk et al., *J. Am. Chem. Soc.*, 122, 2156 (2000).
Wilk et al., *J. Org. Chem.*, 67, 6430-6438 (2002).
Wilk et al., *Tetrahedron Letters*, 42, 5635-5639 (2001).
Wincott, *Current Protocols in Nucleic Acid Chemistry*, vol. 1 (Beaucage S.L., Bergstrom, D.E., Glick, G.D, Jones, R.A. eds); John Wiley and Sons: New York, (2000) pp. 3.5.1-3.5.12.
Yang et al., *Chem. Abs.*, 111, 97382x (1989).
Zhang et al., *Chem. Abs.*, 126(2), 18939t (1997).

* cited by examiner

THERMOLABILE HYDROXYL PROTECTING GROUPS AND METHODS OF USE

CROSS-REFERENCE TO RELATED PATENT APPLICATIONS

This application is a U.S. national phase of International Patent Application No. PCT/US02/38400, filed on Dec. 3, 2002, which published as WO 03/048179 A2 on Jun. 12, 2003, and which claims the benefit of U.S. Provisional Patent Application No. 60/336,745, filed on Dec. 3, 2001.

FIELD OF THE INVENTION

This invention pertains to thermolabile hydroxyl protecting groups and their use in organic synthesis.

BACKGROUND OF THE INVENTION

Protecting groups and associated deprotection methods are widely used in organic synthesis. See, e.g., Greene et al., Protective Groups in Organic Synthesis, 3rd Ed., John Wiley & Sons, Inc., New York, N.Y. (1999). Protecting groups are often used to prevent a particular functional group or part of a molecule (e.g., an amine, a carboxylic acid, a hydroxyl, a heterocycle, etc.) from reacting under certain reaction conditions (e.g., a chemical reaction in which an unprotected part of the same molecule undergoes a synthetic transformation). Hydroxyl-protecting groups are among the most commonly used protecting groups and are of great importance in organic synthesis. Hydroxyl-protecting groups are particularly useful in the synthesis of oligonucleotides, which are undergoing rapid development due to their significant potential therapeutic applications.

The therapeutic application of oligonucleotides is based on the selective formation of hybrids between antisense oligonucleotides and complementary nucleic acids, such as messenger RNAs (mRNAs). Such hybrids inhibit gene expression by preventing the translation of mRNAs into proteins. Nuclease-resistant oligonucleotides, such as thioated oligonucleotides, are highly desirable in this regard. The discovery and development of improved methods for synthesizing nuclease-resistant oligonucleotides continue to be important goals in medicinal chemistry research.

The method most commonly used for the synthesis of thioated oligonucleotides is the phosphoramidite method with stepwise sulfurization (see, e.g., U.S. Pat. Nos. 4,415,732; 4,668,777; 4,973,679; 4,845,205; and 5,525,719). Alternatively, oligonucleotides can be synthesized using an N-acylphosphoramidite method with stepwise sulfurization (see WO 00/56749). In such methods, each coupling step typically is performed with a hydroxyl-protected nucleoside phosphoramidite or N-acylphosphoramidite (e.g., a nucleoside or oligonucleotide phosphoramidite or N-acylphosphoramidite bearing a 5'- or a 3-hydroxyl protecting group). After each nucleotide addition cycle, the terminal hydroxyl-protecting group is removed so that the next coupling step can be carried out in succession. Acid-labile hydroxyl-protecting groups in oligonucleotide synthesis are known. Examples of acid-labile hydroxyl-protecting groups are described in U.S. Pat. Nos. 4,415,732; 4,668,777; and 5,705,621. Such hydroxyl-protecting groups require acidic conditions for deprotection, which is particularly disadvantageous when the oligonucleotide is acid-labile or contains one or more acid-labile functional groups. Photolabile hydroxyl-protecting groups have been described, e.g., in U.S. Pat. Nos. 5,889,165 and 5,763,599. However, photolabile hydroxyl-protecting groups require photochemical conditions for their removal, which is particularly disadvantageous when the oligonucleotide is sensitive to these deprotection conditions or contains one or more photosensitive functional groups. In regard, the range of structural oligonucleotide analogs that can be prepared using conventional hydroxyl protecting groups is often limited to those that are stable under the acidic and/or photochemical deprotection conditions.

Accordingly, there is a need for hydroxyl-protecting groups that can be removed under mild conditions, and for methods of using such protecting groups. The invention provides such protecting groups and methods. These and other objects and advantages of the invention, as well as additional inventive features, will be apparent from the description of the invention provided herein.

BRIEF SUMMARY OF THE INVENTION

The invention provides a hydroxyl-protected alcohol, which includes a thermolabile hydroxyl-protecting group. In one embodiment, the hydroxyl-protected alcohol of the present invention includes a compound of the formula R—O—Pg, wherein Pg is a hydroxyl-protecting group of the formula:

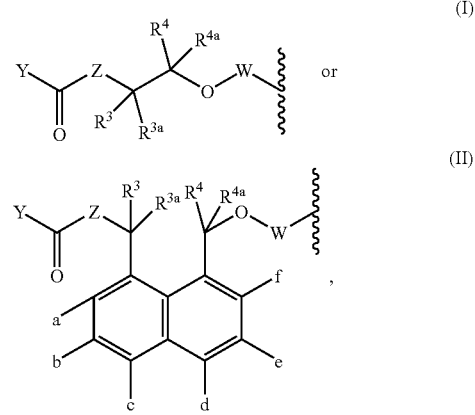

wherein:
Y is $R^1$, $OR^1$, or $NR^1R^{1a}$;
Z is O, $NR^2$ or $CR^2R^{2a}$;
W is CO or SO;
$R^1$, $R^{1a}$, $R^2$, $R^{2a}$, $R^3$, $R^{3a}$, $R^4$ and $R^{4a}$ are the same or different and each is H, a saturated alkyl, an unsaturated alkyl, an aryl, a saturated alkyl comprising an aryl substituent, or an unsaturated alkyl comprising an aryl substituent, wherein:

when $R^1$, $R^{1a}$, $R^2$, $R^{2a}$, $R^3$, $R^{3a}$, $R^4$ or $R^{4a}$ is a saturated alkyl, an unsaturated alkyl, a saturated alkyl comprising an aryl substituent, or an unsaturated alkyl comprising an aryl substituent, the unsaturated alkyl or saturated alkyl is unsubstituted or substituted with one or more substituents, which are the same or different, selected from the group consisting of a halogen, a saturated alkyl, an unsaturated alkyl, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkyl sulfonyl, an aryl sulfonyl, a keto, a thioketo, a cyano, and a nitro;

when $R^1$, $R^{1a}$, $R^2$, $R^{2a}$, $R^3$, $R^{3a}$, $R^4$ or $R^{4a}$ is an aryl, a saturated alkyl comprising an aryl substituent, or an unsaturated alkyl comprising an aryl substituent, the aryl substituent is unsubstituted or substituted with one or more substituents, which are the same or different, selected from the group consisting of a halogen, a saturated alkyl, an unsaturated alkyl, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkylsulfonyl, an arylsulfonyl, a keto, a thioketo, a cyano, a nitro, an amino, an alkylamino and a dialkylamino; and optionally, $R^1$ or $R^{1a}$ is attached to a solid support;

a, b, c, d, e and f are the same or different and each is H, a halogen, a saturated alkyl, an unsaturated alkyl, a hydroxyl, an alkoxy, an aryloxy, an aralkoxy, a cyano, a nitro, a sulfhydryl, an alkyl sulfide, an aryl sulfide, an alkyl sulfoxide, an aryl sulfoxide, an alkylsulfonyl, an arylsulfonyl, a keto, a thioketo, an ester, an amide, an amino, an alkylamino or a dialkylamino; and R is the organic residue of the hydroxyl-protected alcohol; provided that Y is not $OR^1$ when Z is O. In another embodiment, the present invention provides a hydroxyl-protected alcohol which comprises a thermally cleavable 2-amidoethoxycarbonyl hydroxyl-protecting group.

The present invention also provides a method of deprotecting a hydroxyl-protected alcohol. The method comprises heating the hydroxyl-protected alcohol of the present invention at a temperature effective to cleave thermally the hydroxyl-protecting group there from, so as to deprotect the hydroxyl-protected alcohol.

The present invention still further provides a method of producing an oligonucleotide. The method comprises:

(a) reacting a nucleophile of the formula $R^{6a}$—O—$Q^1$—OH with an electrophile to produce an adduct of the formula:

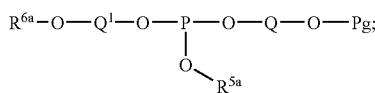

(b) reacting the adduct obtained in step (a) with a reagent selected from the group consisting of oxidizing agents, sulfurizing agents, and selenizing agents to produce a hydroxyl-protected oligonucleotide of the formula:

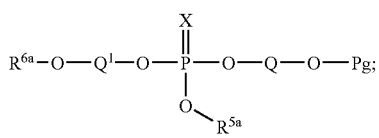

(c) heating the hydroxyl-protected oligonucleotide obtained in step (b) at a temperature effective to cleave Pg to produce a nucleophile;

(d) optionally repeating steps (a)-(c) to produce an oligomer of the formula:

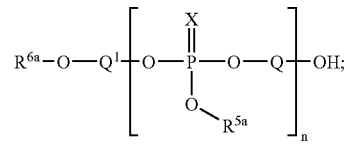

(e) optionally removing $R^{5a}$; and (f) optionally removing $R^{6a}$;

wherein:

Pg is a thermolabile hydroxyl-protecting group as defined in claim 1;

n is an integer from 1 to about 300;

$R^{5a}$ is a protecting group;

$R^{6a}$ is a protecting group or a solid support;

Q and $Q^1$ are the same or different and each is a nucleoside, an oligonucleotide comprising from 2 to about 300 nucleosides, or an oligomer comprising from 2 to about 300 nucleosides;

X is O, S or Se; and, when n is greater than 1, each Q is independently selected.

DETAILED DESCRIPTION OF THE INVENTION

Figure 1:
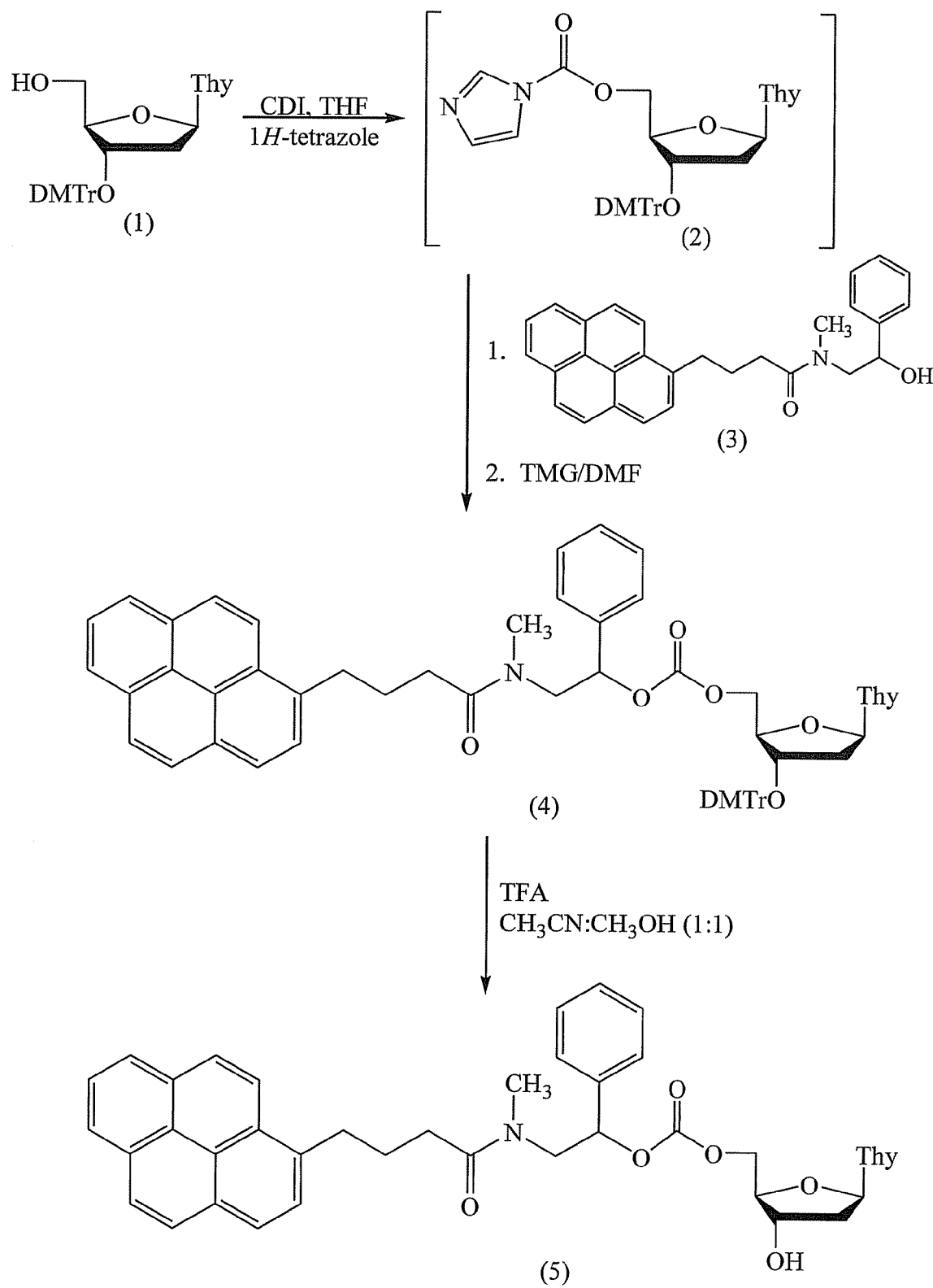
FIG. 1 illustrates the synthesis of a nucleoside in which the 5'-hydroxyl is protected with an exemplary thermolabile hydroxyl-protecting group.

The present invention is predicated on the surprising and unexpected discovery of a novel class of hydroxyl-protecting groups that can be cleave thermallyd without the use of harsh chemicals such as, e.g., acids or bases. In one embodiment, the present invention provides a hydroxyl-protected alcohol of the formula R—O—Pg, wherein Pg is a thermolabile protecting group of the formula:

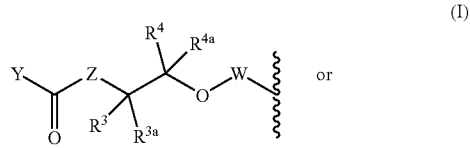

(I)

-continued

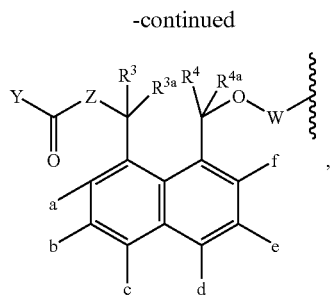
(II)

wherein:
Y is $R^1$, $OR^1$, or $NR^1R^{1a}$,
Z is O, $NR^2$ or $CR^2R^{2a}$;
W is CO or SO;
$R^1$, $R^{1a}$, $R^2$, $R^{2a}$, $R^3$, $R^{3a}$, $R^4$ and $R^{4a}$ are the same or different and each is H, a saturated alkyl, an unsaturated alkyl, an aryl, a saturated alkyl comprising an aryl substituent, or an unsaturated alkyl comprising an aryl substituent, wherein:

when $R^1$, $R^{1a}$, $R^2$, $R^{2a}$, $R^3$, $R^{3a}$, $R^4$ or $R^{4a}$ is a saturated alkyl, an unsaturated alkyl, a saturated alkyl comprising an aryl substituent, or an unsaturated alkyl comprising an aryl substituent, the unsaturated alkyl or saturated alkyl is unsubstituted or substituted with one or more substituents, which are the same or different, selected from the group consisting of a halogen, a saturated alkyl, an unsaturated alkyl, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkylsulfonyl, an arylsulfonyl, a keto, a thioketo, a cyano, and a nitro;

when $R^1$, $R^{1a}$, $R^2$, $R^{2a}$, $R^3$, $R^{3a}$, $R^4$ or $R^{4a}$ is an aryl, a saturated alkyl comprising an aryl substituent, or an unsaturated alkyl comprising an aryl substituent, the aryl substituent is unsubstituted or substituted with one or more substituents, which are the same or different, selected from the group consisting of a halogen, a saturated alkyl, an unsaturated alkyl, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkylsulfonyl, an arylsulfonyl, a keto, a thioketo, a cyano, a nitro, an amino, an alkylamino and a dialkylamino; and optionally, $R^1$ or $R^{1a}$ is attached to a solid support;

a, b, c, d, e and f are the same or different and each is H, a halogen, a saturated alkyl, an unsaturated alkyl, a hydroxyl, an alkoxy, an aryloxy, an aralkoxy, a cyano, a nitro, a sulfhydryl, an alkyl sulfide, an aryl sulfide, an alkyl sulfoxide, an aryl sulfoxide, an alkylsulfonyl, an arylsulfonyl, a keto, a thioketo, an ester, an amide, an amino, an alkylamino and a dialkylamino; and R is the organic residue of the hydroxyl-protected alcohol; provided that Y is not $OR^1$ when Z is O.

In one embodiment, the protecting group of the present invention comprises a protecting group of formula (I) or (II), wherein Z is $NR^2$. In another embodiment, the protecting group of the present invention comprises a protecting group of formula (I) or (II), wherein $R^2$ is H or a saturated alkyl. In yet another embodiment, the protecting group of the present invention comprises a protecting group of formula (I) or (II), wherein Y is a saturated alkyl or an aryl.

Preferably, the protecting group of the present invention comprises a protecting group of formula (I) or (II), wherein $R^3$ and $R^{3a}$ are H. In a preferred embodiment, the protecting group of the present invention comprises a protecting group of formula (I) or (II), wherein $R^4$ and $R^{4a}$ are H, or one of $R^4$ and $R^{4a}$ is H and the other is an aryl. In another preferred embodiment, the protecting group of the present invention comprises a protecting group of formula (I) or (II), wherein W is CO.

In another embodiment, the present invention provides a hydroxyl-protected alcohol which comprises a thermally cleavable 2-amidoethoxycarbonyl hydroxyl-protecting group.

Exemplary protecting groups of the present invention include protecting groups of the formulae:

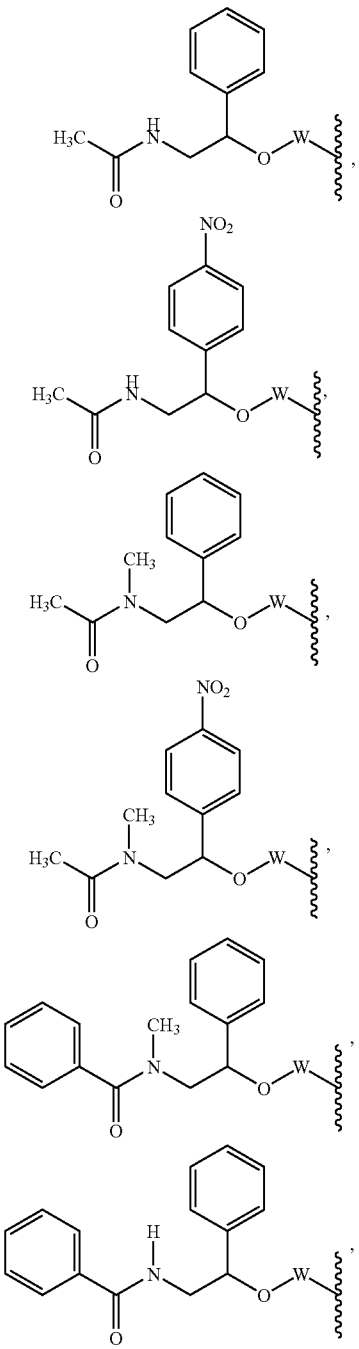

-continued

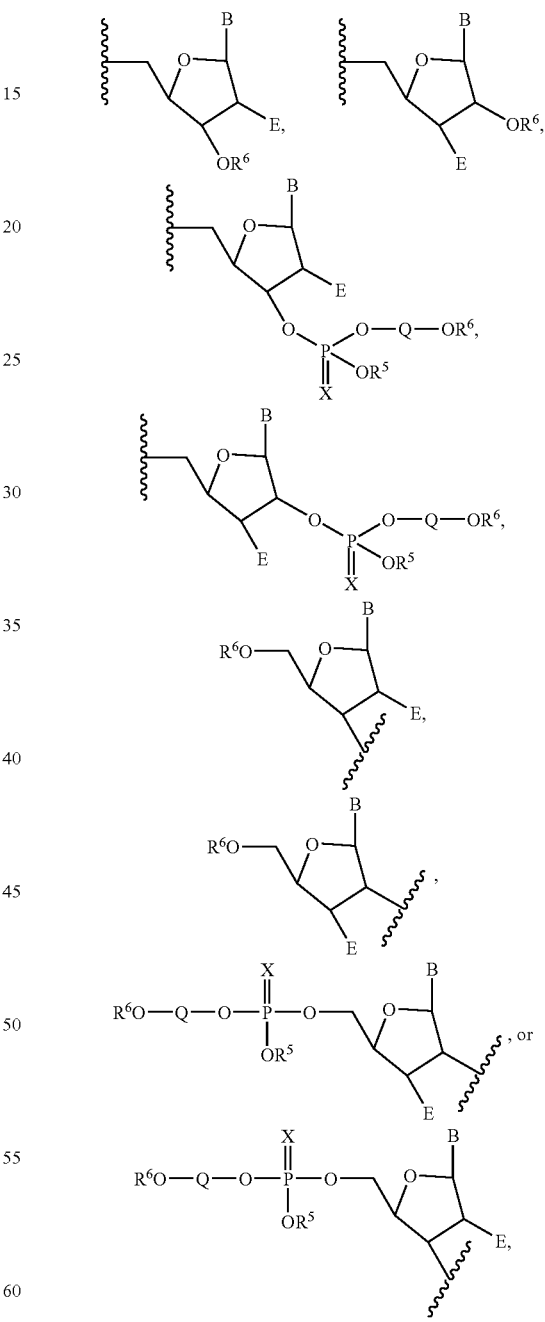

For these exemplary protecting groups, it is preferred that W is CO.

The thermolabile protecting group of the present invention can be used for the protection of any suitable alcohol. Suitable alcohols can range from relatively simple alcohols such as, e.g, low molecular weight aliphatic alcohols, to low molecular weight aromatic alcohols, and the like, to relatively complex alcohols such as, e.g., polyols, sterols, saccharides, nucleic acids, and the like. For instance, the protecting group of the present invention can be used as a hydroxyl-protecting group for nucleosides, oligonucleotides and oligomers that comprise a nucleoside. Such compounds are particularly useful in oligonucleotide synthesis. In one embodiment, the present invention provides a hydroxyl-protected alcohol of the formula R—O—Pg, wherein Pg is as defined herein and R is a nucleoside, an oligonucleotide comprising from 2 to about 300 nucleosides, or an oligomer comprising from 2 to about 300 nucleosides. For such compounds, R is preferably of the formula:

wherein:

Q is a nucleoside, an oligonucleotide comprising from 2 to about 300 nucleosides, or an oligomer comprising from 2 to about 300 nucleosides;

X is O, S or Se;

R[5] is H or a protecting group;

R[6] is H, a protecting group or a solid support;

B is a labeling group, a saturated alkyl, an unsaturated alkyl, a cycloalkyl, an aryl, a heteroaryl comprising from 5 to about 10 atoms in the ring skeleton thereof, a heterocycloalkyl comprising from 3 to about 10 atoms in the ring skeleton thereof, a saturated alkyl comprising an aryl substituent, a unsaturated alkyl comprising an aryl substituent, an amino, an alkylamino, a dialkylamino, a purine, a pyrimidine, adenine, guanine, cytosine, uracil, or thymine, wherein B is unsubstituted or substituted with one or more substituents, which are the same or different, selected from the group consisting of a nucleobase protecting group, R[7], OR[7], NHR[7], NR[7]R[8], an amidine (e.g., N=CH—NR[7a]R[8a], N=C(alkyl)-NR[7a]R[8a], and the like), CN, NO$_2$, N$_3$, and a halogen, wherein R[7] and R[8] are the same or different and each is H, a saturated alkyl, an unsaturated alkyl, a keto or a thioketo, and R[7a] and R[8a] are the same or different and each is a saturated alkyl or an unsaturated alkyl, or, R[7a] and R[8a], together with the nitrogen atom to which they are bonded, form a heterocycle containing from 3 to about 7 atoms in the ring skeleton thereof; and E is H, a halogen, OR[9], NHR[9], or NR[9]R[10], wherein R[9] and R[10] are the same or different and each is H, a protecting group, a saturated alkyl, an unsaturated alkyl, a keto, or a thioketo.

In a preferred embodiment, R is of the formula:

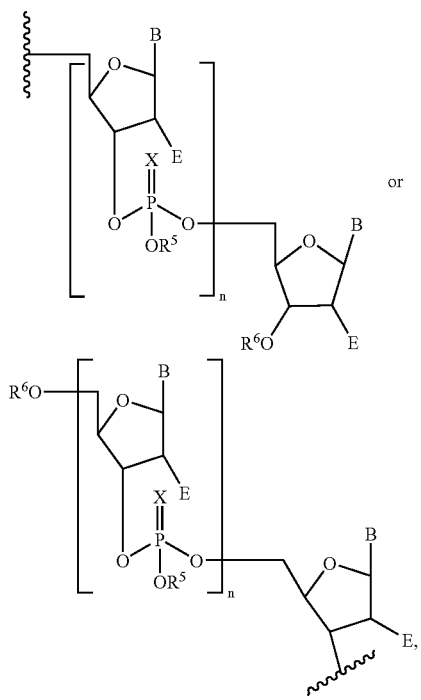

wherein n is an integer from 0 to about 300.

Suitable B substituents can include heterocycles that are commonly used in oligonucleotide synthesis such as, for example, substituents selected from the group consisting of a purine, a pyrimidine, adenine, guanine, cytosine, uracil, and thymine. Suitable nucleosides can include nucleosides that are commonly used in oligonucleotide synthesis such as, for example, nucleosides of the formula:

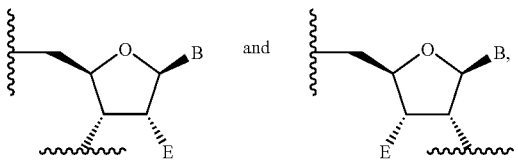

wherein B and E are as defined herein.

The present invention further provides a method of deprotecting a hydroxyl-protected alcohol. The method comprises heating the hydroxyl-protected alcohol of the present invention at a temperature effective to cleave thermally the hydroxyl-protecting group there from, so as to deprotect the hydroxyl-protected alcohol. The deprotection method of the present invention can further comprise synthetically modifying the hydroxyl-protected alcohol prior to deprotection. Such synthetic modifications can include, for example, oxidation reactions, reduction reactions, rearrangement reactions, coupling reactions, fragmentation reactions, addition reactions, complexation reactions, catalytic reactions, displacement reactions, enzymatic reactions, and the like.

Desirably, the temperature effective to cleave thermally the hydroxyl-protecting group is lower than the temperature at which the alcohol (the protected alcohol or the unprotected alcohol) degrades in the reaction system. It will be appreciated that the temperature effective to cleave thermally the hydroxyl-protecting group can vary depending on the structure of the protecting group, the structure of the alcohol that is protected, and environmental factors such as, e.g., solvent, pH, pressure, concentration, other reactants, other reagents, by products, and the like. It will also be appreciated that the degradation temperature of the alcohol (protected or unprotected) also can vary depending on the structure of the alcohol and environmental factors such as, e.g., solvent, pH, pressure, concentration, other reactants, other reagents, by products, and the like.

Any suitable temperature can be used in accordance with the deprotection method of the present invention. For example, the temperature effective to cleave thermally the hydroxyl-protecting group can range from about 20-150° C., from about 30-120° C., from about 40-100° C., from about 50-90° C., from about 60-90° C., from about 70-90° C., and the like.

If desired, the deprotection method of the present invention can be carried out in a fluid medium, e.g., in the presence of a solvent. Suitable solvents can include, for example, organic solvents and aqueous solvents. Organic solvents can include, for example, alcohols, aliphatic hydrocarbons, aromatic hydrocarbons, ketones, ethers, and the like. Aqueous solvents can include, for example, water, mixtures of water and an organic solvent (e.g., water/alcohol mixtures, water/acetonitrile mixtures, water/acetone mixtures), and the like. Preferably, the solvent is an aqueous solvent. Exemplary aqueous solvents include water, water/acetonitrile mixtures, water/ethanol mixtures, and the like.

As indicated above, the protecting group of the present invention can be removed without the use of acids, bases or other harsh reagents. Preferably, the deprotection method of the present invention is carried out from about pH 5.5-7.5, preferably from about pH 6.0-7.5, more preferably from about pH 6.5-7.5, and most preferably from about pH 7.0-7.5. If desired, a suitable buffer (e.g., a phosphate buffer such as PBS or the like) can be used to stabilize the pH.

The deprotection method of the present invention is particularly useful in oligonucleotide synthesis. In one embodiment, the method of producing an oligonucleotide comprises:

(a) reacting a nucleophile of the formula $R^{6a}$—O—$Q^1$—OH with an electrophile to produce an adduct of the formula:

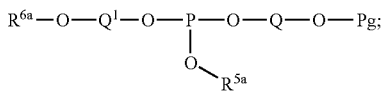

(b) reacting the adduct obtained in step (a) with a reagent selected from the group consisting of oxidizing agents, sulfurizing agents, and selenizing agents to produce a hydroxyl-protected oligonucleotide of the formula:

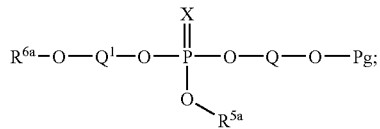

(c) heating the hydroxyl-protected oligonucleotide obtained in step (b) at a temperature effective to cleave Pg to produce a nucleophile;

(d) optionally repeating steps (a)-(c) to produce an oligomer of the formula:

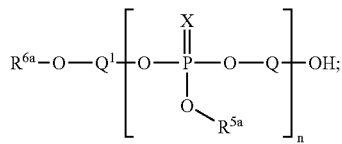

(e) optionally removing $R^{5a}$; and
(f) optionally removing $R^{6a}$;

wherein:

Pg is a thermolabile hydroxyl-protecting group as defined herein;

n is an integer from 1 to about 300;

$R^{5a}$ is a protecting group;

$R^{6a}$ is a protecting group or a solid support;

Q and $Q^1$ are the same or different and each is a nucleoside, an oligonucleotide comprising from 2 to about 300 nucleosides, or an oligomer comprising from 2 to about 300 nucleosides;

X is O, S or Se; and, when n is greater than 1, each Q is independently selected.

Step (c) can be carried out in accordance with the deprotection method of the present invention described herein. Preferably, the temperature effective to cleave Pg in step (c) of the method of the present invention is below about 100° C. More preferably, the temperature in step (c) is from about 40-90° C., and is even more preferably from about 50-90° C. In a preferred embodiment, step (c) is carried out in a solvent, which is preferably an aqueous solvent. Exemplary aqueous solvents include water, water/acetonitrile mixtures, water/ethanol mixtures, and the like. Desirably, a suitable buffer, e.g., a phosphate buffer, is used in step (c).

The term "saturated alkyl" means a straight-chain or branched-chain saturated alkyl containing, e.g., from 1 to about 20 carbon atoms, for example, from 1 to about 10 carbon atoms, from 1 to about 8 carbon atoms, or from 1 to about 6 carbon atoms. Examples of saturated alkyls include methyl, ethyl, propyl, isopropyl, n-butyl, sec-butyl, octadecyl, and the like. Saturated alkyl substituents can be unsubstituted or substituted, for example, with at least one substituent selected from the group consisting of a halogen, a nitro, an amino, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkyl sulfonyl, an aryl sulfonyl, a keto, a thioketo, an alkyl, a cyano, and the like.

The term "unsaturated alkyl" means an unsaturated alkyl (straight-chain or branched-chain), as defined herein, in which at least one single carbon-carbon bonds thereof is instead a multiple bond, for example, a double bond or a triple bond. Unsaturated alkyls include alkenyls and alkynyls, as well as substituents that have a combination of double and triple bonds. The term "alkenyl" means a straight-chain or branched-chain alkenyl having one or more double bonds. An alkenyl can contain, e.g., from 2 to about 20 carbon atoms, for example, from 2 to about 10 carbon atoms, from 2 to about 8 carbon atoms, or from 2 to about 6 carbon atoms. Examples of alkenyls include vinyl, allyl, 1,4-butadienyl, isopropenyl, and the like. The term "alkynyl" means a straight-chain or branched-chain alkynyl having one or more triple bonds. An alkynyl can contain, e.g., from 2 to about 20 carbon atoms, for example, from 2 to about 10 carbon atoms, from 2 to about 8 carbon atoms, or from 2 to about 6 carbon atoms. Examples of alkynyls include ethynyl, propynyl (propargyl), butynyl, and the like. Unsaturated alkyl substituents can be unsubstituted or substituted, for example, with at least one substituent selected from the group consisting of a halogen, a nitro, an amino, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkyl sulfonyl, an aryl sulfonyl, a keto, a thioketo, an alkyl, a cyano and the like.

The term "aryl" means an aromatic carbocyclic radical, as commonly understood in the art, and includes monocyclic and polycyclic aromatics. The aryl substituent preferably comprises 6-14 carbon atoms in the carbocyclic skeleton thereof. Examples of aryl substituents include, but are not limited to, phenyl, naphthyl and the like, which are unsubstituted or substituted with one or more substituents selected from the group consisting of a halogen, a saturated alkyl, an unsaturated alkyl, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkylsulfonyl, an arylsulfonyl, a keto, a thioketo, a cyano, a nitro, an amino, an alkylamino, a dialkylamino, and the like.

A saturated alkyl comprising an aryl substituent means an alkyl substituent in which at least one hydrogen atom thereof is substituted with an aryl substituent (an aralkyl). Examples of saturated alkyls comprising an aryl substituent include, but are not limited to, benzyl, phenethyl, 2-phenyl-1-propyl, 3,4-diphenylbutyl and the like.

An unsaturated alkyl comprising an aryl substituent means an unsaturated alkyl substituent in which at least one hydrogen atom thereof is substituted with an aryl (an aralkenyl or an aralkinyl). Examples of unsaturated alkyls comprising an aryl substituent include, but are not limited to, 2-phenylethenyl, 2-phenylethinyl, 4-naphthyl-2-butynyl and the like.

The term "alkoxy" means a saturated alkyl or an unsaturated alkyl in which at least one hydrogen atom thereof is substituted with an oxygen atom. Examples of alkoxy substituents include, but are not limited to, methoxy, ethoxy, isopropoxy, 2-butenyloxy, and the like.

The term "aryloxy" means an aryl in which at least one hydrogen atom thereof is substituted with an oxygen atom. Examples of aryloxy substituents include, but are not limited to, phenoxy, naphthoxy and the like.

The term "aralkoxy" means an aralkyl, an aralkenyl or an aralkinyl in which at least one hydrogen atom thereof is substituted with an oxygen atom. Examples of aralkoxy substituents include, but are not limited to, benzyloxy, 4-phenyl-n-butoxy, 4-phenyl-2-butene-1-yloxy, and the like.

The term "ester" means a carboxylic acid or an analog thereof in which an acidic proton is replaced by an organic radical such as, for example, a saturated alkyl, an unsaturated alkyl, an aryl, an aralkyl or the like. Examples of esters include, but are not limited to, alkyl carboxylates (e.g., ethoxycarbonyl and tert-butyloxycarbonyl), unsaturated alkyl carboxylates (e.g., allyloxycarbonyl), aryl carboxylates (e.g., phenoxycarbonyl and benzyloxycarbonyl) and thioesters (e.g., benzylthiocarbonyl), and the like.

The term "amide" means aminocarbonyl and analogous substituents. Examples of amides include, but are not limited to, N-alkyl amides (e.g., ethylaminocarbonyl, diethylaminocarbonyl, and tert-butylaminocarbonyl), unsaturated N-alkyl amides and analogous substituents (e.g., allylaminocarbonyl), N-aryl amides and analogous substituents (e.g., phenylaminocarbonyl and benzylaminocarbonyl) and thioamides (e.g., benzylaminothiocarbonyl), and the like.

The term "alkyl sulfide" means a saturated or an unsaturated alkyl in which at least one hydrogen atom thereof is substituted with a sulfur atom. Examples of alkyl sulfides include, but are not limited to, methylthio, ethylthio, isopropylthio, 2-butenylthio, and the like.

The term "aryl sulfide" means an aryl in which at least one hydrogen atom thereof is substituted with a sulfur atom. Examples of aryl sulfides include, but are not limited to, phenylthio, naphthylthio and the like. The term "alkyl sulfoxide" means a saturated or an unsaturated alkyl in which at least one hydrogen atom thereof is substituted with a sulfoxide (SO). Examples of alkyl sulfoxides include, but are not limited to, methylsulfoxy, ethylsulfoxy, isopropylsulfoxy, 2-butenylsulfoxy, and the like.

The term "alkyl sufoxide" means a saturated or an unsaturated alkyl in which at least one hydrogen atom thereof is substituted with a sulfoxide (SO). Examples of alkyl sulfoxides include, but are not limited to, methylsulfoxy, ethylsulfoxy, isopropylsulfoxy, 2-butenylsulfoxy, and the like.

The term "aryl sulfoxide" means an aryl in which at least one hydrogen atom thereof is substituted with a sulfoxide. Examples of aryl sulfoxides include, but are not limited to, phenylsulfoxy, naphthylsulfoxy and the like.

The term "alkylsulfonyl" means a saturated or an unsaturated alkyl in which at least one hydrogen atom thereof is substituted with a sulfonyl ($SO_2$). Examples of alkylsulfonyls include, but are not limited to, methylsulfonyl, ethylsulfonyl, isopropylsulfonyl, 2-butenylsulfonyl, and the like.

The term "arylsulfonyl" means an aryl in which at least one hydrogen atom thereof is substituted with a sulfonyl. Examples of arylsulfonyl substituents include, but are not limited to, phenylsulfonyl, naphthylsulfonyl and the like.

The term "keto" means a carbonyl which is substituted with an organic radical such as, for example, a saturated alkyl, an unsaturated alkyl, an aryl, an aralkyl, or the like. Examples of keto substituents include, but are not limited to, alkylcarbonyls (e.g., ethylcarbonyl and tert-butylcarbonyl), unsaturated alkyl carbonyls (e.g., allylcarbonyl), aryl carbonyls (e.g., phenylcarbonyl and benzylcarbonyl), and the like.

The term "thioketo" means a keto in which the carbonyl oxygen is substituted with a sulfur atom. Examples of thioketo substituents include, but are not limited to, alkyl thiocarbonyls (e.g., ethyl thiocarbonyl and tert-butyl thiocarbonyl), unsaturated alkyl thiocarbonyls (e.g., allyl thiocarbonyl), aryl thiocarbonyls (e.g., phenyl thiocarbonyl and benzyl thiocarbonyl), and the like.

The term "alkylamino" means an amino which is substituted with one saturated or unsaturated alkyl substituent. Examples of alkylamino substituents include, but are not limited to, methylamino, ethylamino, isopropylamino, 2-butenylamino, and the like.

The term "dialkylamino" means an amino which is substituted with two alkyl substituents, which are the same or different and which can be saturated or unsaturated. Examples of dialkylamino substituents include dimethylamino, diethylamino, ethylisopropylamino, diisopropylamino, di-2-butenylamino and the like.

The term "cycloalkyl" means a monocycloalkyl or a polycycloalkyl which comprises one or more aliphatic carbocyclic rings, which are the same or different. Typically, the cycloalkyl has from 3 to about 10 carbon atoms in the carbocyclic skeleton of each ring. Preferably, the cycloalkyl has from about 4-7 carbon atoms, more preferably from about 5-6 carbons atoms in each ring. Examples of monocyclic cycloalkyls include cyclopropyl, cyclobutyl, cyclopentyl, cyclohexyl, cyclohexenyl, cycloheptyl, cyclodecyl, and the like. Examples of polycyclic cycloalkyls include decahydronaphthyl, bicyclo[5.4.0]undecyl, adamantyl, and the like.

The terms heterocycle and heterocyclic refer to heterocycloalkyls and heteroaryls. The term "heterocycloalkyl" means a cycloalkyl in which at least one carbon in the ring skeleton thereof is substituted with a heteroatom such as, for example, O, N, S, an oxide of N, an oxide of S, and the like. The heterocycloalkyl optionally has one or more double bonds within one or more of its rings, and may include a non-aromatic or an aromatic ring. The heterocycloalkyl preferably has from 3 to about 10 atoms (members) in the skeleton of each ring, more preferably from about 5-10 atoms, still more preferably from about 4-7 atoms, and most preferably 5-6 atoms. Examples of heterocycloalkyls include epoxy, aziridyl, oxetanyl, tetrahydrofuranyl, ribose, dihydrofuranyl, piperidinyl, piperazinyl, pyranyl, morpholinyl, and the like.

The term "heteroaryl" means an aromatic heterocyclic ring as commonly understood in the art, including monocyclics such as, for example, imidazolyl, thiazolyl, pyrazolyl, pyrrolyl, furanyl, pyrazolinyl, thiophenyl, oxazolyl, isoxazolyl, pyridinyl, pyridonyl, pyrimidinyl, cytosinyl, 5-methylcytosinyl, thyminyl, pyrazinyl, and triazinyl, and polycyclics such as, for example, quinolinyl, isoquinolinyl, indolyl, purinyl, adeninyl, guaninyl, $N^6$-methyladeninyl, benzothiazolyl, and the like. The heteroaryl can be unsubstituted or substituted with one or more substituents, which are the same or different, selected from the group consisting of the aryl substituents described herein, and the like. The heteroaryl preferably has from 3 to about 10 atoms (members) in the ring skeleton of each ring, more preferably from about 4-7 atoms, and most preferably 5-6 atoms.

It will be appreciated that the heterocycloalkyl and heteroaryl substituents can be bonded via a heteroatom, such as nitrogen (e.g., 1-imidazolyl), or via a carbon atom (e.g., 2-imidazolyl and 4-thiazolyl). It will also be appreciated that the heteroaryls are not necessarily "aromatic" to the same extent as a benzene ring, although heteroaryls can nonetheless demonstrate physical and chemical properties associated with aromaticity, as commonly understood in the art.

The term "nucleoside" includes naturally occurring and modified nucleosides, including all forms of furanosides found in nucleic acids. Naturally occurring nucleosides include, for example, adenosine, guanosine, cytidine, thymidine, and uridine.

Nucleoside "derivatives" or "analogs" include synthetic nucleosides and intermediates that are useful for the preparation thereof, e.g., as described herein. Nucleoside derivatives also include nucleosides having modified base moieties, with or without protecting groups. Such analogs include, for example, deoxyinosine, 2,6-diaminopurine-2'-deoxyriboside, 5-methyl-2'-deoxycytidine, and the like. The base rings most commonly found in naturally occurring nucleosides are purine and pyrimidine rings. Naturally occurring purine rings include, for example, adenine, guanine, and $N^6$-methyladenine. Naturally occurring pyrimidine rings include, for example, cytosine, thymine, and 5-methylcytosine. The compounds and methods of the present invention include such base rings and synthetic analogs thereof, as well as unnatural heterocycle-substituted base sugars, acyclic-substituted base sugars, and the like. Moreover, nucleoside derivatives include other purine and pyrimidine derivatives, for example, halogen-substituted purines (e.g., 6-fluoropurine), halogen-substituted pyrimidines (e.g., 5-fluoro uracil), $N^6$-ethyladenine, $N^6$-(alkyl)-cytosines, 5-ethylcytosine, and the like.

The term "oligonucleotide" includes oligomers (e.g., linear oligomers) of natural or modified nucleosides, modified oligonucleotides, and the like. Oligonucleotides include deoxyribonucleosides, ribonucleosides, anomeric forms thereof, and the like. Oligonucleotides are typically linked by phoshodiester bonds, or the equivalent thereof, ranging in size from a few monomeric units (e.g., 2-4) to several hundred monomeric units. Exemplary oligonucleotides that can be used in accordance with the present invention include oligomers of naturally-occurring nucleosides, e.g., ranging in length from about 12 to about 60 monomeric units, or from about 15 to about 30 monomeric units. Whenever an oligonucleotide is represented by a sequence of letters, such as "AGTC" it will be appreciated that the nucleotides are in the 5'-to-3'-orientation from left to right.

In accordance with the present invention, Q and/or $Q^1$ can be a natural nucleoside or a modified/unnatural nucleoside. Q and/or $Q^1$ also can be an oligomer comprising one or more natural or modified/unnatural nucleosides. Modified nucleosides can be obtained, for example, by any suitable synthetic method known in the art for preparing nucleosides, derivatives, or analogs thereof. Modified nucleosides include, but are not limited to, chemically modified nucleosides used as building blocks for "labeled" oligonucleotides, or suitable precursors or analogs used in the preparation of such modified nucleosides. Various chemically modified nucleosides are described, for example, in Smith et al., Nucleosides & Nucleotides, 15(10), 1581-1594 (1996) ("Smith et al."). Smith et al. describes the synthesis of nucleosides (and oligomers which include such nucleosides) in which the base ring is replaced by a carboxylic acid. Various "labeling" groups (e.g., biotin, cholesterol, fluorenylmethoxycarbonyl (Fmoc), and trifluoroacetyl) can be appended to the carboxylic acid, e.g., via a modified amide linker. Modified nucleosides also include other chemically modified nucleosides, for example, nucleosides described in Smith et al. in which the base ring is replaced by a hydroxyethyl, a cyano, a carboxylic acid (including esters and amides thereof), or the like. Modified nucleosides further include nucleosides in which the base ring is replaced by a cyclic substituent, for example, an aryl, a cycloalkyl, a heterocycloalkyl, a heteroaryl (other than a base naturally occurring in nucleosides), or the like.

Q and $Q^1$ also include oligonucleotides, which can be natural or modified. Modified oligonucleotides include, for example, oligonucleotides containing a modified nucleoside, oligonucleotides containing a modified internucleotide linkage, oligonucleotides having any combination of modified nucleosides and internucleotide linkages (even if a natural nucleoside is present in the oligomer chain), or the like. Oligonucleotides which include one or more nucleosides that are connected via modified internucleotide linkages are described, for example, in Waldner et al., Bioorg. Med. Chem. Letters, 6, 19, 2363-2366 (1996) ("Waldner et al."), which describes the synthesis of oligonucleotides containing various amide internucleotide linkages.

The term "oligomer comprising a nucleoside" means an oligomer in which at least one of the monomeric units comprises one or more nucleosides, and at least one of the other monomeric units is not a nucleoside. For example, one of the monomeric units in the oligomer can be an amino acid, an organic spacer (e.g., an aliphatic spacer, an aromatic spacer, an alkylene glycol, a carbohydrate (e.g., a sugar), or the like. Moreover, one or more of the non-nucleoside units of the oligomer can be oligomeric, for example, a peptide, an oligosaccharide, a polyalkylene glycol, or the like.

It will be appreciated that protecting groups (sometimes referred to as blocking groups), other than the thermolabile protecting group of the present invention, can be utilized in accordance with the present invention. Protecting groups can include substituents, functional groups, salts, ligands, and the like, which are bonded (e.g., via covalent bond, ionic bond, complex, or the like) to a potentially reactive functional group. As indicated above, protecting groups can be used to prevent a potentially reactive functional group from reacting under certain reaction conditions. Preferably, the protecting group is stable under the reaction conditions employed, and is removable under mild deprotection conditions. It will be appreciated that protecting groups should be chosen based on the type of substituent that is being protected, the structure of the molecule for which the protecting group is used, the reaction conditions used, the type of solvent used, the conditions required for removing the protecting group, and the like. One of skill in the art may choose different protecting groups to protect different functional groups such as, e.g., phosphites, phosphates, amines, thiols, hydroxyls, and the like. Reaction conditions that influence the choice of protecting group can typically include the pH, the temperature, the relative reactivities of the reactants and/or products, and the like.

Protecting groups for hydroxyls can include, for example, silyl ethers (e.g., trimethylsilyl, triethylsilyl, tert-butyldimethylsilyl, tert-butyldiphenylsilyl, dimethylphenylsilyl, and diphenylmethylsilyl), benzyl carbonates, trityl, monomethoxytrityl, dimethoxytrityl, esters (e.g., acetate, benzoate, and the like), pixyl, tert-butyloxycarbonyl, 9-fluorenylmethyloxycarbonyl (Fmoc), a tetrahydropyranyl group, photolabile protecting groups and the like. When the hydroxyl is a sugar hydroxyl, suitable protecting groups can include, for example, pixyl, acetyl, 9-fluorenylmethyloxycarbonyl (Fmoc), t-butyldimethylsilyl (TBDMS), trityl, monomethoxytrityl ("MMT" or "MMTr"), dimethoxytrityl ("DMT" or "DMTr"), and the like. Protecting groups for nitrogen include, for example, amides (e.g., trifluoroacetyl, acetyl, phenoxyacetyl, benzoyl, and isobutyryl), carbamates (e.g., tert-butyloxycarbonyl, (4-nitrophenyl)ethyloxycarbonyl, and N-benzyloxycarbonyl), trityl, amidines and the like. These are defined in the literature: see, e.g., Iyer, *Current Protocols in Nucleic Acid Chemistry*, Vol. 1 (Beaucage S. L., Bergstrom, D. E., Glick, G. D. Jones R. A. eds); John Wiley and Sons: New York, 2000, pp. 2.1.1-2.1.17; Beaucage, et al., *Tetrahedron*, 48, 2223-2311 (1992); and McBride et al., *J. Am. Chem. Soc.*, 108, 2040-2048 (1986).

Suitable internucleosidic phosphorus protecting groups can include, for example, those described in U.S. Pat. Nos. 4,417,046, 5,705,621, 5,571,902, and 5,959,099. Suitable internucleosidic phosphorus protecting groups also can include those obtained from oligonucleotide synthesis using N-acylphosphoramidite precursors, e.g., as described in WO 00/56749. Suitable internucleosidic phosphorus protecting groups also can include thermolabile internucleosidic phosphorus protecting groups as described in U.S. patent application Ser. No. 09/792,799 (filed on Feb. 23, 2001); Grajkowsli et al., *Organic Lett.* 3, 1287-1290 (2001); and Wilk et al. *Tetrahedron Lett.*, 42, 5635-5639 (2001).

Suitable protecting groups also can include, for example, 2-[N,N-(dialkylamino)oxy]ethyl (Prakash et al., *Org. Lett.*, 2, 2995-3998 (2000)), a (2-methoxy)ethoxy (Martin, *Helv. Chim. Acta.*, 78, 486-504 (1995)), triisopropylsilyloxymethyl, protecting groups defined by Wincott, *Current Protocols in Nucleic Acid Chemistry*, Vol. 1 (Beaucage S. L., Bergstrom, D. E., Glick, G. D. Jones R. A. eds); and John Wiley and Sons: New York, 2000, pp. 3.5.1-3.5.12, and the like.

Any suitable solid support can be used in accordance with the present invention. Solid supports are commonly known in the art and include, for example, organic solid supports (e.g., crosslinked polystyrene), inorganic solid supports (e.g., silica supports), and like. Preferably, the solid support is an inorganic support, which is more preferably a silica support. It will be appreciated that the solid support can include linkers, spacers, arms, and other moieties (organic and inorganic moieties) known in the art for manipulating attachment to a solid support. It will also be appreciated that the solid support can be bonded to the molecule directly, without the use of linkers, spacers, arms, or other connecting moieties. Some aspects of the invention are common with known approaches to solid phase synthesis of oligonucleotides, for example, selection of suitable protecting groups, selection of suitable solid phase supports, and the like. Consequently, considerable guidance in making such selections in the context of the present invention can be found in literature, e.g. Beaucage et al., *Tetrahedron*, 49, 6123-6194 (1993).

Oxidizing agents that can be used in accordance with the present invention include any suitable reagent that can oxidize a tricoordinated phosphorus atom, particularly a phosphite, to provide a phosphorus atom having a valence of greater than three, preferably a tetracoordinated phosphorus atom such as, for example, a phosphate, or an equivalent thereof. Suitable oxidizing agents include, for example, $I_2/H_2O$, peroxides, such as tert-butylhydroperoxide, and the like.

Sulfurizing agents that can be used in accordance with the present invention include any suitable reagent that can sulfurize a tricoordinated phosphorus atom, particularly a phosphite, to provide a phosphorus atom with a valence of greater than three, preferably a tetracoordinated phosphorus atom such as, for example, a phosphorothioate, or an equivalent thereof. Suitable sulfurizing agents include, for example, 3H-1,2-benzodithiol-3-one 1,1-dioxide ("Beaucage Reagent"), phenylacetyl disulfide, bis(O,O-diisopropoxyphosphinothioyl) disulfide, and the like.

Selenizing agents that can be used in accordance with the present invention include any suitable reagent that can selenize a tricoordinated phosphorus atom, particularly a phosphite, to provide a phosphorus atom having a valence of greater than three, preferably a tetracoordinated phosphorus atom such as a phosphoroselenoate, or an equivalent thereof. Suitable selenizing agents include, for example, potassium selenocyanate (KSeCN), elemental selenium and the like.

EXAMPLES

The following examples further illustrate the invention but, of course, should not be construed as in any way limiting its scope.

Example 1

This example demonstrates the preparation of 5'-O-[2-[N-(1-pyrenylbutryl)-N-methyl]amino-1-phenylethyl]oxycarbonyl thymidine (5) (FIG. 1).

To 3'-O-(4,4'-dimethoxytrityl)thymidine (1) (680 mg, 1.25 mmol), 1,1'-carbonyldiimidazole (162 mg, 1.25 mmol), and 1H-tetrazole (175 mg, 2.5 mmol) in a flame-dried 4 mL glass vial, stoppered with a rubber septum, was added by syringe 2.5 mL of dry THF. The resulting solution is stirred at 25° C. for 1 h. TLC [EtOAc-hexane (7:3)] shows only a small amount of unreacted (1) (ca. 10-15%).

To the pyrenylamidobenzyl alcohol (3) (525 mg, 1.25 mmol) in a separate 4 mL flame-dried glass vial, stoppered with a rubber septum, was added by syringe tetramethylguanidine (TMG) (0.785 mL, 6.25 mmol), which had been dried over a 4 Å molecular sieves, and dry DMF (1 mL). The suspension was heated with a heat gun until a solution was obtained. The solution was then added by syringe to the CDI-activated nucleoside (2). The resulting brownish solution was stirred at 25° C. for 18 h. The reaction product (4) (two diastereomers) moves slower than (3) and slightly faster than (1) on silica gel TLC [EtOAc-hexane (7:3)]. The brownish solution was purified on 10 preparative TLC plates (silica gel 60, Whatman, 20×20 cm, 1 mm thick plates). The plates were developed using EtOAc-hexane (1:1) just above the base line. This process was repeated three times.

The plates were further developed twice using EtOAc-hexane (1:1) and then once using EtOAc-hexane (7:3). Bands were cut-off and the product (4) was eluted from silica gel using EtOAc-MeOH (1:1). Solvent and volatiles were removed under reduced pressure and the remaining material was dissolved in 10 mL of MeCN:MeOH (1:1). TFA (0.100 mL) was added and the rate of detritylation was monitored within 15 min by TLC. TFA was added at the rate of 0.050 mL at every 15 min until the detritylation was complete. The reaction mixture was evaporated to an oil and coevaporated twice with MeOH (10 mL). The resulting oil was dissolved with a minimum MeCN—$CHCl_3$ (1:2) and loaded onto a 3 cm×12 cm silica gel 60 (230-400 mesh) column equilibrated in MeCN—$CHCl_3$ (1:2). The product (5) was eluted from the column using MeCN—$CHCl_3$ (1:2) and then MeCN—$CHCl_3$ (1:1). Evaporation of the solvent afforded (5) as an off-white foam (232 mg, 0.34 mmol, 27%).

Example 2

Figure 2:
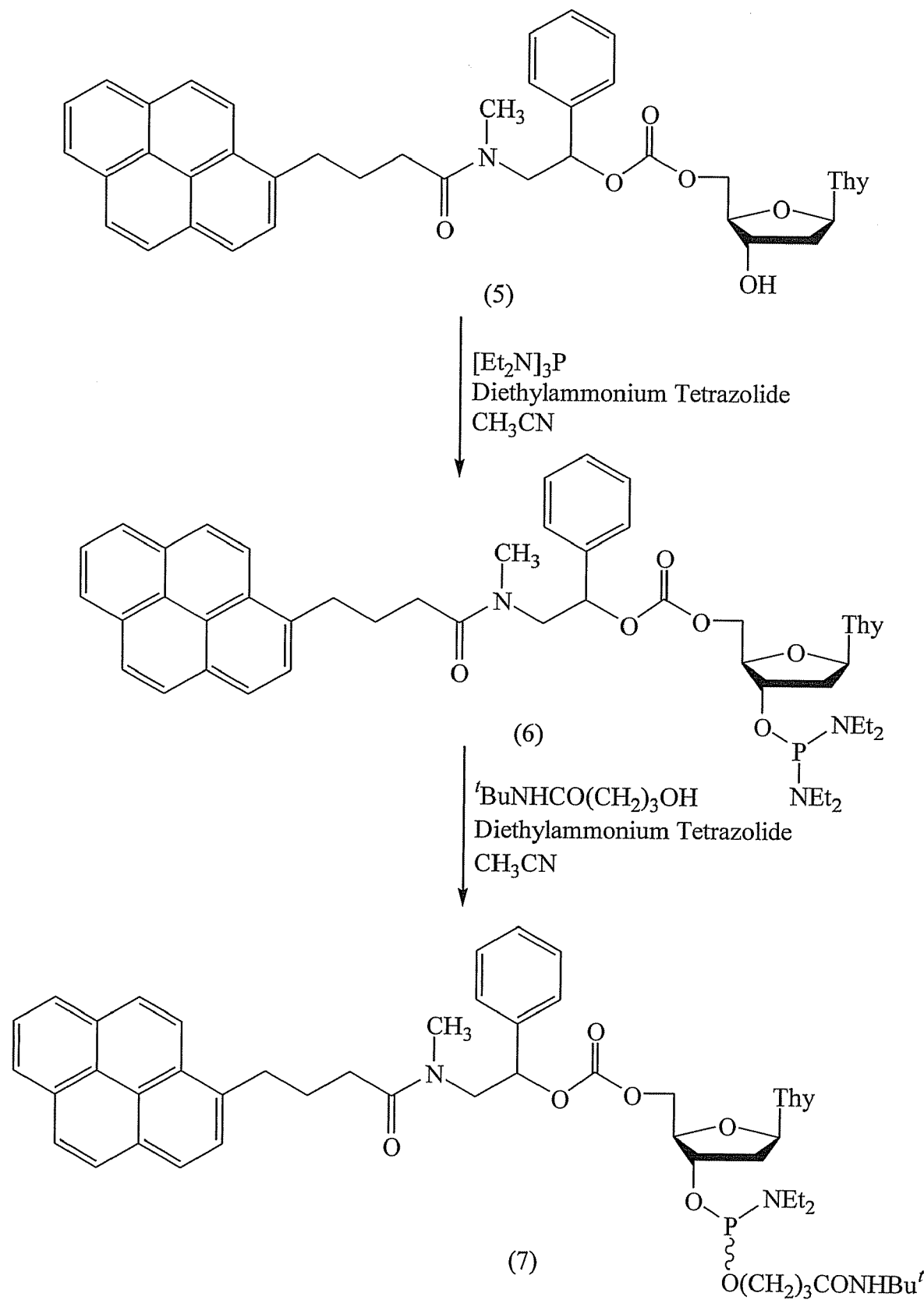
FIG. 2 illustrates the synthesis of a nucleoside phosphoramidite protected with a thermolabile hydroxyl-protecting group.

This example demonstrates the preparation of 5'-O-[2-[N-(1 pyrenylbutyryl)-N-methyl]amino-1-phenylethyl]oxycarbonyl-3'-O-(3-tert-butylaminocarbonyl)propyl-1-oxy-N,N-diethylaminophosphinyl thymidine ((7), FIG. 2).

Equimolar amounts of (5) (0.25 nmol), hexaethylphosphorus triamide, and diethylammonium tetrazolide were mixed in dry methylene chloride (1.25 mL) for 30 min at 25° C. The deoxyribonucleoside 3'-O-phosphordiamidite (6) generated in situ was then reacted with an equimolar amount of 3-(tert-butylaminocarbonyl)propan-1-ol, and the reaction mixture was left stirring for at least 6 h at ambient temperature. The resulting deoxyribonucleoside phosphoramidite (7) was purified by silica gel chromatography and isolated as a white foam (~90% yield).

Example 3

Figure 3:
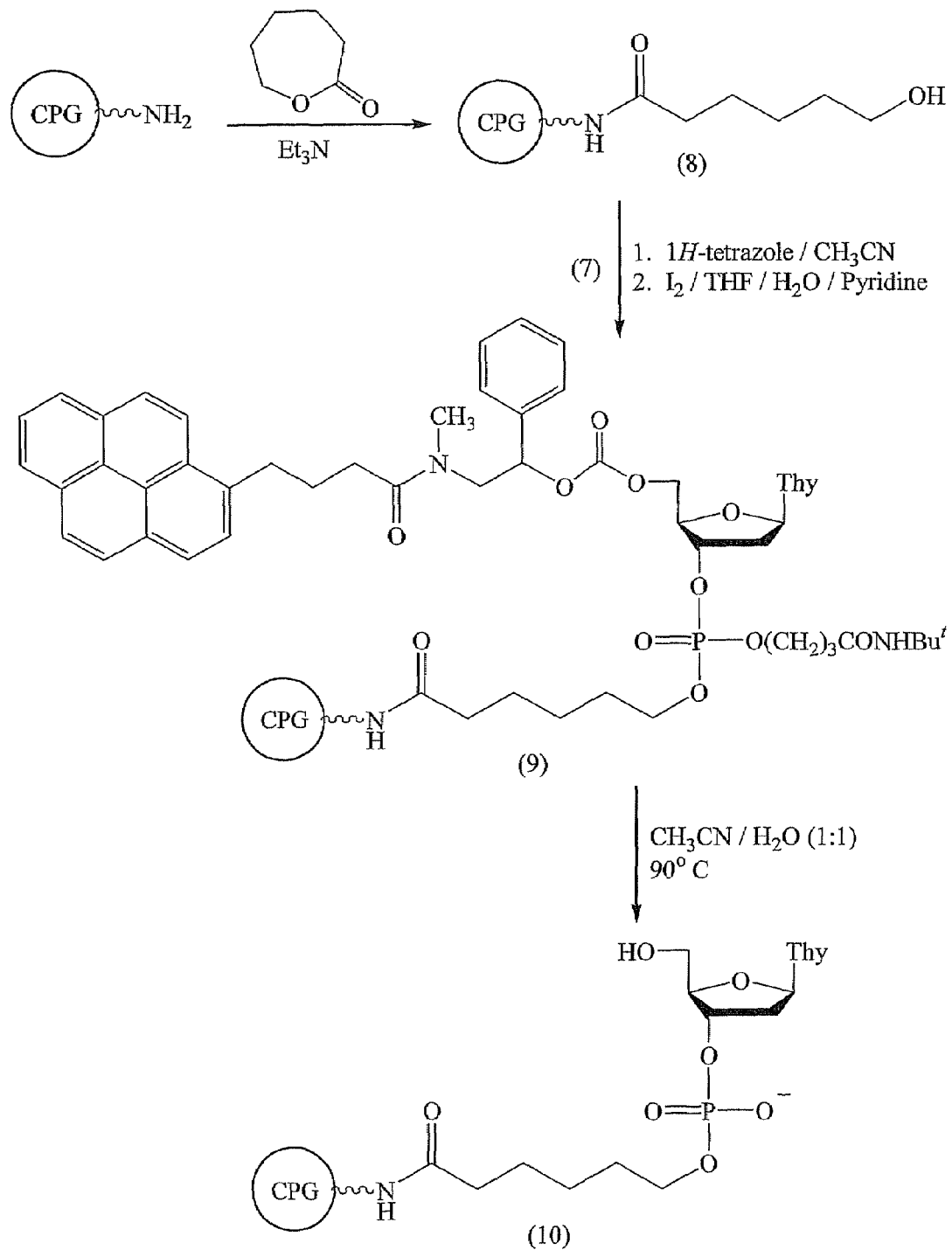
FIG. 3 illustrates the synthesis and thermal deprotection of a nucleoside bonded to a solid support.

This example demonstrates the preparation and thermal deprotection of a nucleoside bound to CPG support (FIG. 3).

Commercial LCAA-CPG (0.5 g) was washed with triethylamine and then reacted with ε-caprolactone (3 mL) for 3 days at 25° C. The support was then washed with MeOH, MeCN, and then dried under vacuum to afford (8).

The coupling of the pyrenyl deoxyribonucleoside phosphoramidite (7) to the CPG support (8) was performed as follows. To dry LCAA-CPG support (8) (~10 mg) and dry pyrenyl deoxyribonucleoside phosphoramidite (7) (20 μmol) was added a 0.4 M solution of 1H-tetrazole in acetonitrile (0.200 mL). The suspension was gently shaken for 3 min and thoroughly washed with acetonitrile. The support was treated with a 0.02 M solution of iodine in THF:water:pyridine for 2 min and exhaustively washed with THF, MeOH, and MeCN to afford the functionalized support (9).

Cleavage of the 5'-O-protecting group from (9) (FIG. 3) was performed as follows. The functionalized support (9) (~10 mg) was placed into a 1 mL-quartz cuvette, suspended in 1 mL MeCN—$H_2O$ (1:1) and heated to 90° C. Release of the pyrenylamido benzyl alcohol (3) was monitored by UV at 342 μm. The protecting group was cleaved to the extent of greater than 99% within 1.8 h at 90° C.

Example 4

Figure 4:
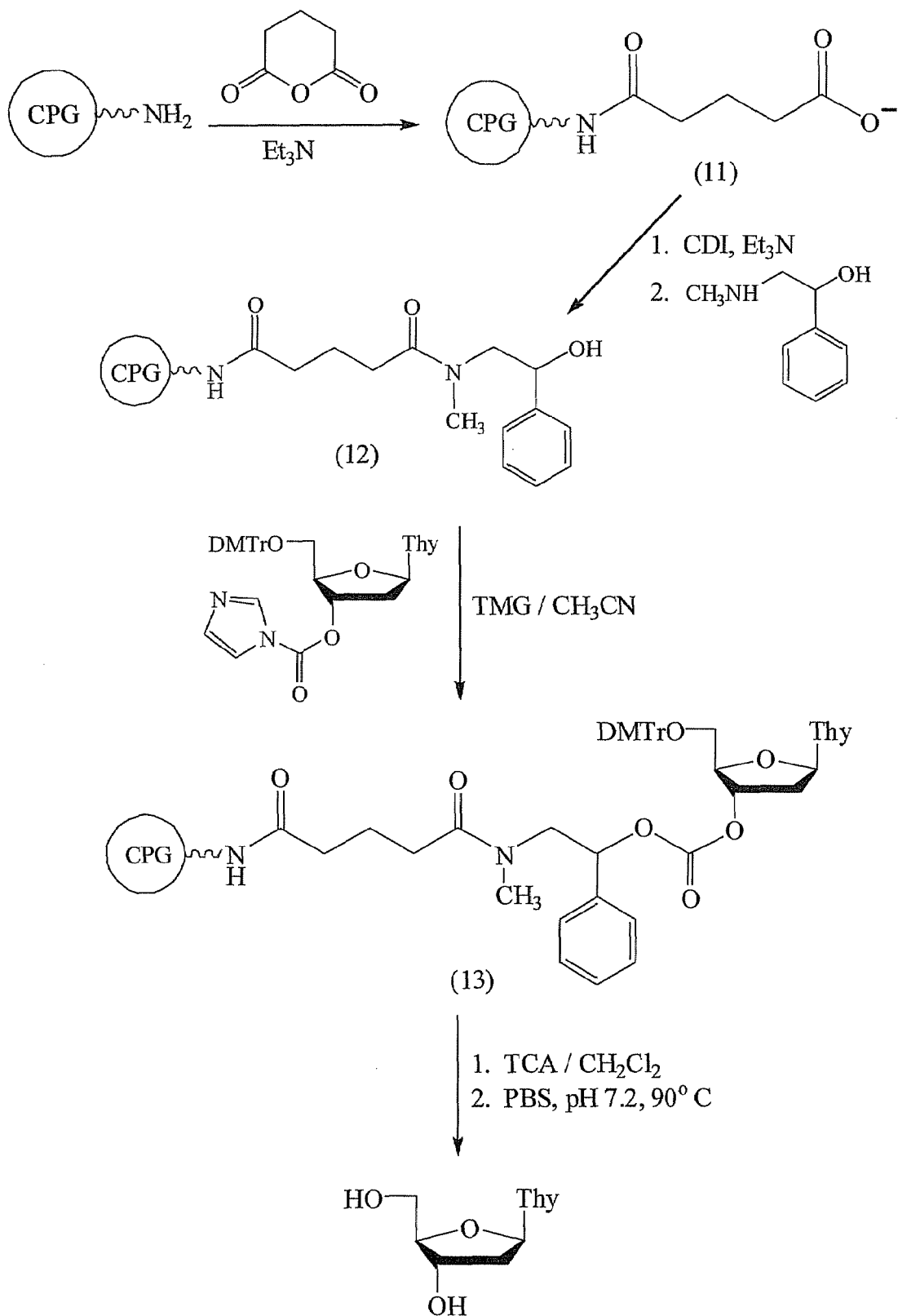
FIG. 4 illustrates the synthesis and thermal deprotection of a nucleoside protected with a thermolabile hydroxyl-protecting group which is bonded to a solid support.

This example demonstrates the preparation and thermal deprotection of a nucleoside bearing a thermolabile hydroxyl-protecting group which is bound to a CPG support (FIG. 4).

Commercial Aminopropylated-CPG (1 g) was washed with triethylamine and reacted with a solution of glutaric anhydride (200 mg) in pyridine (6 mL) for 12 h at 25° C., to afford (11). The support (11) was then washed with MeOH, MeCN, and then dried under vacuum. Treatment of (11) with a 0.1 M solution of 1,1'-carbonyldiimidazole in MeCN for 2 h at 25° C., followed by a thorough wash with MeCN, and reaction with a 0.1 M solution of α-(methylaminomethyl)benzyl alcohol for at least 12 h at 25° C., afforded the functionalized support (12).

To 5'-O-(4,4'-dimethoxytrityl)thymidine (1 mmol) in dry MeCN (3 mL) was added 1,1'-carbonyldiimidazole (1 mmol). The reaction was allowed to react at 25° C. until disappearance of the starting material is almost complete (<5%). This solution was then added to dry support (12) along with tetramethylguanidine (6 mmol). The suspension was allowed to react for at least 12 h at 25° C. The nucleoside-derived support (13) was carefully washed with acetonitrile, treated with 3% trichloracetic acid in methylene chloride for 5 min, washed with acetonitrile, and dried under vacuum.

The nucleoside-derived support (13) (~10 mg) was placed into a 1 mL-quartz cuvette, suspended in 1 mL PBS buffer (pH 7.2) and heated to 90° C. The release of thymidine was monitored by UV at 260 μm. The nucleoside was cleaved from (13) to the extent of greater than 99% within 47 min at 90° C. When this reaction was performed at ambient temperature less than 1% of thymidine was released from (13) over a period of 4 h and less than 6% over 18 h.

Example 5

Figure 5:
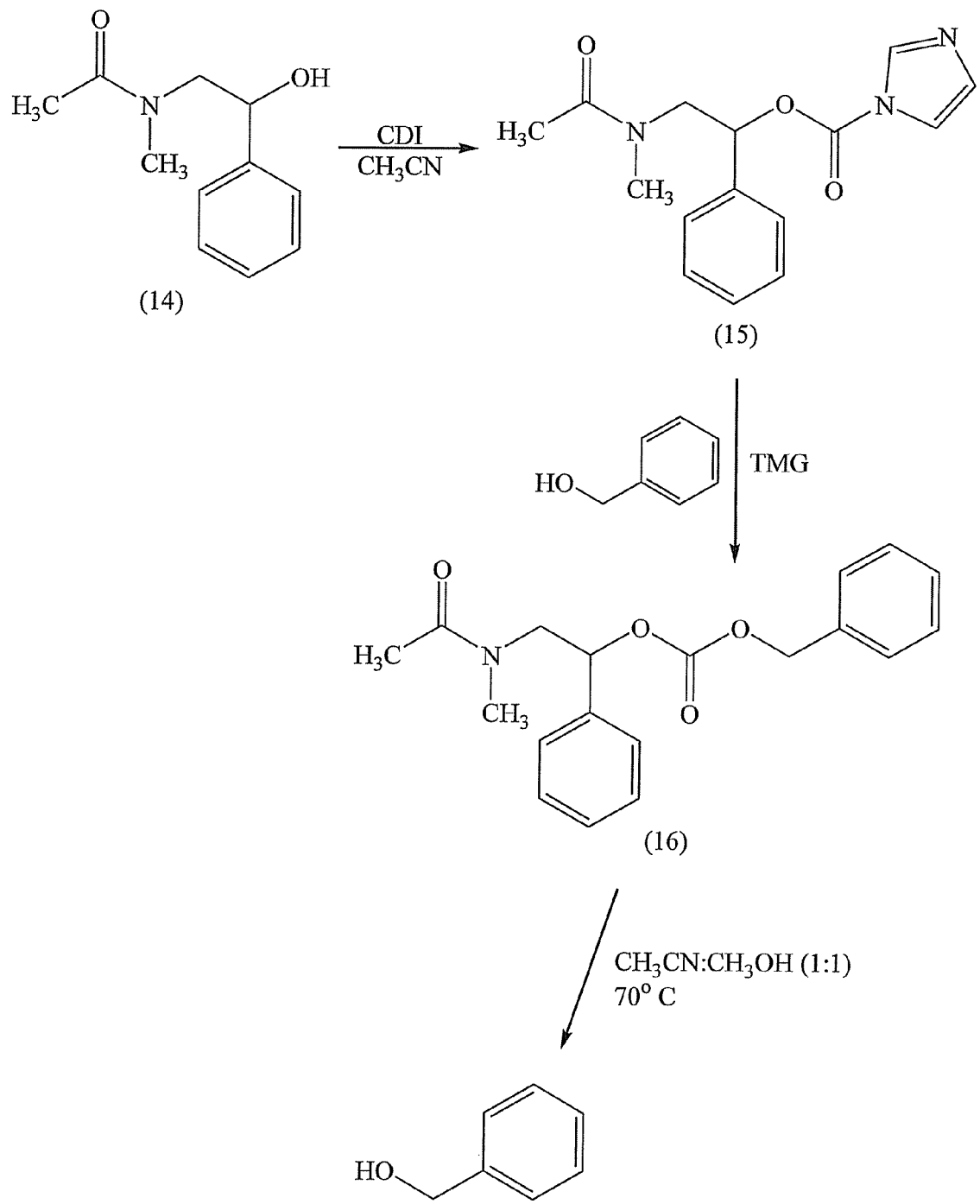
FIG. 5 illustrates the synthesis and thermal deprotection of benzyl alcohol.

This example demonstrates the preparation of benzyl-[2-(N-acetyl-N-methyl)amino-1-phenylethyl] carbonate (16) and the thermal deprotection thereof (FIG. 5).

2-(N-acetyl-N-methyl)-1-phenylethanol ((14), 41.4 mg, 0.2 mmol) was dissolved in dry aceonitrile (1 mL) in a 4 mL screw cap vial. To this solution was slowly added 1,1'-carbonyldiimidazole in dry acetonitrile (1 mL). TLC analysis (EtOAc:petroleum ether 9:1) indicates that the reaction was complete within 2 h at 25° C. Benzyl alcohol (0.02 mL, 0.2 mmol) was then added to the solution followed by tetramethylguanidine (TMG, 0.14 mL). TLC analysis of the reaction (EtOAc:petroleum ether (9:1) and dichloromethane:methanol (9:1)) showed the disappearance of the imidazolide intermediate (15) and the appearance of a new product (16) over a period of 2 h. The reaction mixture was applied onto one preparative TLC plate (Whatman, PK6F Silica Gel 60 Å, 20×20 cm, 1 mm thickness). The plate was developed once in dichloromethane:methanol (9:1 v/v). The product was isolated by eluting it out of the appropriate silica gel band with dichloromethane:methanol (9:1 v/v). Yield: 22 mg (35%).

The benzyl carbonate (16) (~10 mg) was dissolved in $CD_3CN:D_2O$ (2:1, v/v) in a NMR tube and heated at 70° C. The release of benzyl alcohol was monitored by NMR spectroscopy. It took about 24 h for complete release of benzyl alcohol from (16).

As a control experiment, dibenzyl carbonate in $CD_3CN$:$D_2O$ (2:1, v/v) is heated at 90° C.

The release of benzyl alcohol was monitored by NMR at various time points. After 8 days under these conditions less than 1% of benzyl alcohol could be detected. The release of benzyl alcohol from (16) is therefore not caused by simple hydrolysis of the carbonate function.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A hydroxyl-protected alcohol of the formula R—O—Pg, wherein Pg is a hydroxyl-protecting group of the formula:

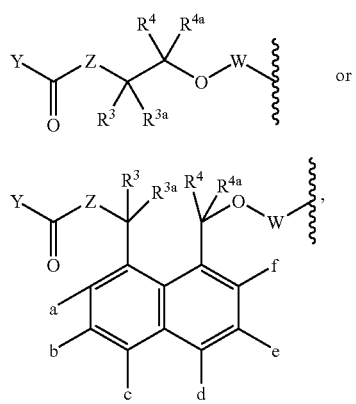

wherein:
Y is $R^1$, $OR^1$, or $NR^1R^{1a}$;
Z is O, $NR^2$ or $CR^2R^{2a}$;
W is CO;
$R^1$, $R^{1a}$, $R^2$, $R^{2a}$, $R^3$, $R^{3a}$, $R^4$ and $R^{4a}$ are the same or different and each is H, a saturated alkyl, an unsaturated alkyl, an aryl, a saturated alkyl with an aryl substituent, or an unsaturated alkyl with an aryl substituent, wherein:
any of the alkyl-containing groups for $R^1$, $R^{1a}$, $R^2$, $R^{2a}$, $R^3$, $R^{3a}$, $R^4$ or $R^{4a}$ is unsubstituted or substituted with one or more substituents, which are the same or different, and selected from the group consisting of a halogen, a saturated alkyl, an unsaturated alkyl, a hydroxyl, an alkoxy, an aryloxy, an aralkoxy, an alkyl carboxylate, an unsaturated alkyl carboxylate, an aryl carboxylate, an amide, a sulfhydryl, an alkyl sulfide, an aryl sulfide, an alkyl sulfoxide, an aryl sulfoxide, an alkyl sulfonyl, an aryl sulfonyl, an alkylcarbonyl, an unsaturated alkyl carbonyl, an aryl carbonyl an alkyl thiocarbonyl, an unsaturated alkyl thiocarbonyl, an aryl thiocarbonyl, a cyano, and a nitro;
any of the aryl-containing groups for $R^1$, $R^{1a}$, $R^2$, $R^{2a}$, $R^3$, $R^{3a}$, $R^4$ or $R^{4a}$ is unsubstituted or substituted with one or more substituents, which are the same or different, and selected from the group consisting of a halogen, a saturated alkyl, an unsaturated alkyl, a hydroxyl, an alkoxy, an aryloxy, an aralkoxy, an alkyl carboxylate, an unsaturated alkyl carboxylate, an aryl carboxylate, an amide, a sulfhydryl, an alkyl sulfide, an aryl sulfide, an alkyl sulfoxide, an aryl sulfoxide, an alkylsulfonyl, an arylsulfonyl, an alkylcarbonyl, an unsaturated alkyl carbonyl, an aryl carbonyl, an alkyl thiocarbonyl, an unsaturated alkyl thiocarbonyl, an aryl thiocarbonyl, a cyano, a nitro, an amino, an alkylamino and a dialkylamino; and
optionally, $R^1$ or $R^{1a}$ is attached to a solid support;
a, b, c, d, e and f are the same or different and each is H, a halogen, a saturated alkyl, an unsaturated alkyl, a hydroxyl, an alkoxy, an aryloxy, an aralkoxy, a cyano, a nitro, a sulfhydryl, an alkyl sulfide, an aryl sulfide, an alkyl sulfoxide, an aryl sulfoxide, an alkylsulfonyl, an arylsulfonyl, an alkylcarbonyl, an unsaturated alkyl carbonyl, an aryl carbonyl, an alkyl thiocarbonyl, an unsaturated alkyl thiocarbonyl, an aryl thiocarbonyl, an alkyl carboxylate, an unsaturated alkyl carboxylate, an aryl carboxylate, an amide, an amino, an alkylamino or a dialkylamino; and
R is a nucleosidyl group, an oligonucleotidyl group with 2 to about 300 nucleosides, or an oligomer with 2 to about 300 nucleosides;
provided that Y is not $OR^1$ when Z is O.

2. The hydroxyl-protected alcohol of claim 1, wherein Z is $NR^2$.

3. The hydroxyl-protected alcohol of claim 1, wherein $R^2$ is H or a saturated alkyl.

4. The hydroxyl-protected alcohol of claim 1, wherein Y is $R^1$, wherein $R^1$ is a saturated alkyl or an aryl.

5. The hydroxyl-protected alcohol of claim 1, wherein $R^3$ and $R^{3a}$ are H.

6. The hydroxyl-protected alcohol of claim 1, wherein $R^4$ and $R^{4a}$ are H, or one of $R^4$ and $R^{4a}$ is H and the other is an aryl.

7. The hydroxyl-protected alcohol of claim 1, wherein Pg is selected from the group consisting of:

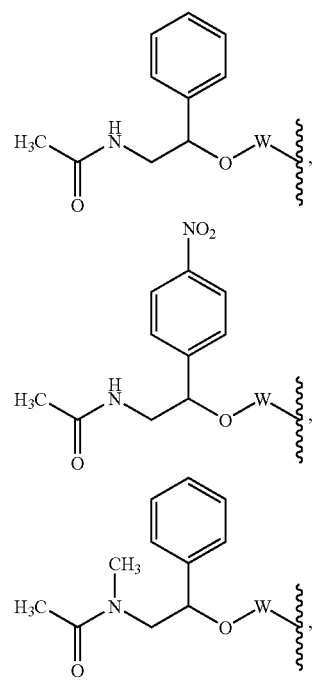

-continued
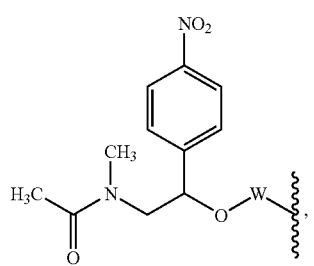
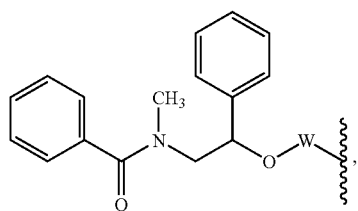
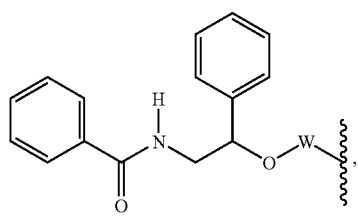
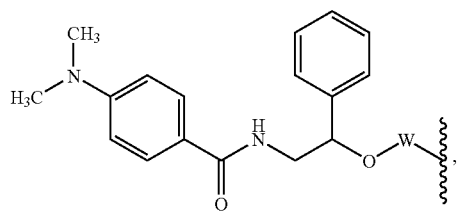
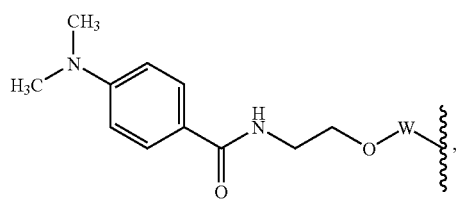
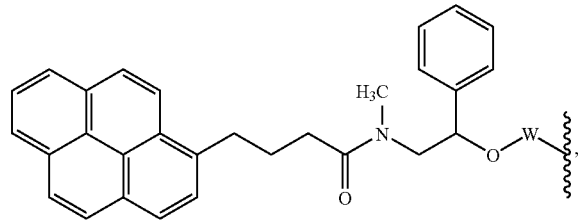
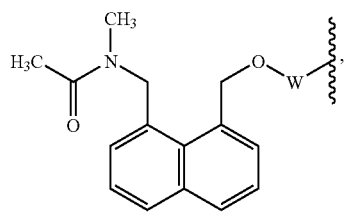
-continued
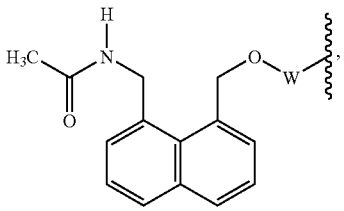
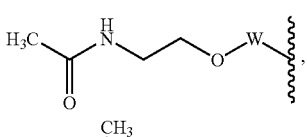
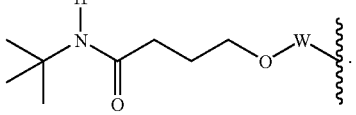
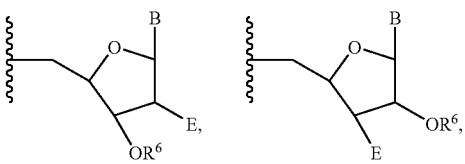
and
8. The hydroxyl-protected alcohol of claim 1, wherein R is of the formula:
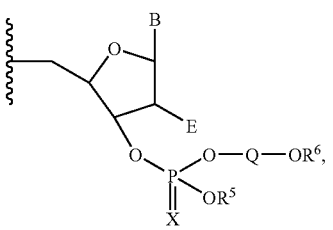
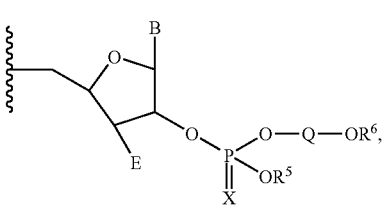
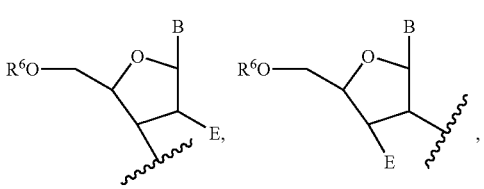

-continued

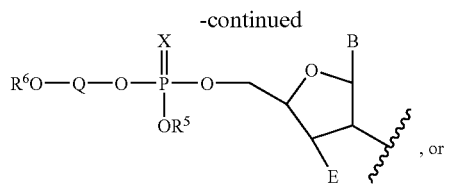
, or

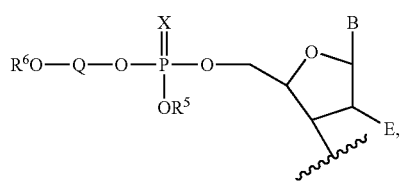

wherein:
Q is a linking substituent selected from the group consisting of nucleosidyl group, an oligonucleotidyl group with 2 to about 300 nucleosides, and an oligomer with 2 to about 300 nucleosides;
X is O, S or Se;
$R^5$ is H or a protecting group;
$R^6$ is H, a protecting group or a solid support;
B is a labeling group, a saturated alkyl, an unsaturated alkyl, a cycloalkyl, an aryl, a heteroaryl with 5 to about 10 atoms, including at least one heteroatom selected from the group consisting of O, N, S, an oxide of N, and an oxide of S in the ring skeleton thereof, a heterocycloalkyl with 3 to about 10 atoms, including at least one heteroatom selected from the group consisting of O, N, S, an oxide of N, and an oxide of S in the ring skeleton thereof, a saturated alkyl with an aryl substituent, an unsaturated alkyl with an aryl substituent, an amino, an alkylamino, a dialkylamino, a purinyl, a pyrimidinyl, adeninyl, guaninyl, cytosinyl, uracilyl, or thyminyl,
wherein B is unsubstituted or substituted with one or more substituents, which are the same or different, selected from the group consisting of a nucleobase protecting group, $R^7$, $OR^7$, $NHR^7$, $NR^7R^8$, N=CH—$NR^{7a}R^{8a}$, N=C(alkyl)-$NR^{7a}R^{8a}$, CN, $NO_2$, $N_3$, and a halogen, wherein $R^7$ and $R^8$ are the same or different and each is H, a saturated alkyl, an unsaturated alkyl, an alkylcarbonyl, an unsaturated alkyl carbonyl, an aryl carbonyl, an alkyl thiocarbonyl, an unsaturated alkyl thiocarbonyl, or an aryl thiocarbonyl, and $R^{7a}$ and $R^{8a}$ are the same or different and each is a saturated alkyl or an unsaturated alkyl, or, $R^{7a}$ and $R^{8a}$, together with the nitrogen atom to which they are bonded, form a heterocycle containing 3 to about 7 atoms in the ring skeleton thereof; and
E is H, a halogen, $OR^9$, $NHR^9$, or $NR^9R^{10}$, wherein $R^9$ and $R^{10}$ are the same or different and each is H, a protecting group, a saturated alkyl, an unsaturated alkyl, an alkylcarbonyl, an unsaturated alkyl carbonyl, an aryl carbonyl, an alkyl thiocarbonyl, an unsaturated alkyl thiocarbonyl, or an aryl thiocarbonyl.

9. The hydroxyl-protected alcohol of claim 1, wherein R is of the formula:

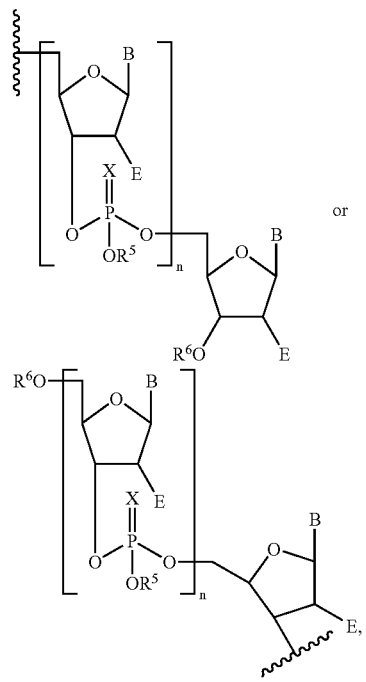

wherein
n is an integer from 0 to about 300;
X is O, S or Se;
$R^5$ is H or a protecting group;
$R^6$ is H, a protecting group or a solid support;
B is a labeling group, a saturated alkyl, an unsaturated alkyl, a cycloalkyl, an aryl, a heteroaryl with 5 to about 10 atoms, including at least one heteroatom selected from the group consisting of O, N, S, an oxide of N, and an oxide of S in the ring skeleton thereof, a heterocycloalkyl with 3 to about 10 atoms, including at least one heteroatom selected from the group consisting of O, N, S, an oxide of N, and an oxide of S in the ring skeleton thereof, a saturated alkyl with an aryl substituent, an unsaturated alkyl with an aryl substituent, an amino, an alkylamino, a dialkylamino, a purinyl, a pyrimidinyl, adeninyl, guaninyl, cytosinyl, uracilyl, or thyminyl,
wherein B is unsubstituted or substituted with one or more substituents, which are the same or different, selected from the group consisting of a nucleobase protecting group $R^7$, $OR^7$, $NHR^7$, $NR^7R^8$, N=CH—$NR^{7a}R^{8a}$ N=C(alkyl)-$NR^{7a}R^{8a}$CN, $NO_1$, $N_3$, and a halogens wherein $R^7$ and $R^8$ are the same or different and each is H, a saturated alkyl, an unsaturated alkyl, an alkylcarbonyl, an unsaturated alkyl carbonyl, an aryl carbonyl, an alkyl thiocarbonyl, an unsaturated alkyl thiocarbonyl, or an aryl thiocarbonyl, and $R^{7a}$ and $R^{8a}$ are the same or different and each is a saturated alkyl or an unsaturated alkyl or, $R^{7a}$ and $R^{8a}$ together with the nitrogen atom to which they are bonded, form a heterocycle containing 3 to about 7 atoms in the ring skeleton thereof; and
E is H, a halogen, $OR^9$, $NHR^9$, or $NR^9R^{10}$, wherein $R^9$ and $R^{10}$ are the same or different and each is H, a protecting group, a saturated alkyl, an unsaturated alkyl alkylcarbonyl, an unsaturated alkyl carbonyl, an aryl carbonyl, an alkyl thiocarbonyl, an unsaturated alkyl thiocarbonyl, or an aryl thiocarbonyl.

10. The hydroxyl-protected alcohol of claim 8, wherein B is selected from the group consisting of a purinyl, a pyrimidinyl, adeninyl, guaninyl, cytosinyl, uracilyl, and thyminyl.

11. A method of deprotecting a hydroxyl-protected alcohol, the method comprising heating the compound of claim 1 at a temperature effective to cleave thermally the Pg protecting Pg group therefrom, so as to deprotect and form the corresponding alcohol R—OH.

12. A method of producing an oligonucleotide, the method comprising:

(a) reacting a nucleophile of the formula $R^{6a}$—O—$Q^1$—OH with an electrophile of the formula Pg—O—Q—O—P(Lg)—O—$R^{5a}$ to produce an adduct of the formula:

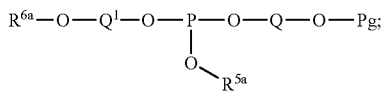

(b) reacting the adduct obtained in step (a) with a reagent selected from the group consisting of oxidizing agents, sulfurizing agents, and selenizing agents to produce a hydroxyl-protected oligonucleotide of the formula:

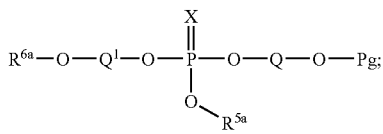

(c) heating the hydroxyl-protected oligonucleotide obtained in step (b) at a temperature effective to cleave Pg to produce a nucleophile;

(d) optionally repeating steps (a)-(c) to produce an oligomer of the formula:

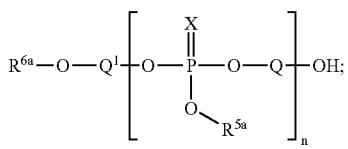

(e) optionally removing $R^{5a}$ by deprotection; and
(f) optionally removing $R^{6a}$;
wherein:
Pg is a hydroxyl-protecting group of the formula:

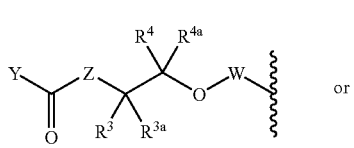

-continued

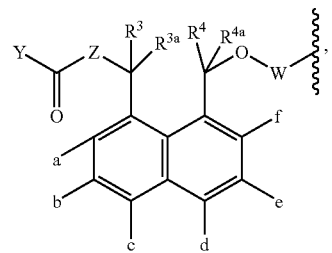

wherein:
Y is $R^1$, $OR^1$, or $NR^1R^{1a}$;
Z is O, $NR^2$ or $CR^2R^{2a}$;
W is CO;
$R^1$, $R^{1a}$, $R^2$, $R^{2a}$, $R^3$, $R^{3a}$, $R^4$ and $R^{4a}$ are the same or different and each is H, a saturated alkyl, an unsaturated alkyl, an aryl, a saturated alkyl with an aryl substituent, or an unsaturated alkyl with an aryl substituent, wherein:
any of the alkyl-containing groups for $R^1$, $R^{1a}$, $R^2$, $R^{2a}$, $R^3$, $R^{3a}$, $R^4$ or $R^{4a}$ is unsubstituted or substituted with one or more substituents, which are the same or different, and selected from the group consisting of a halogen, a saturated alkyl, an unsaturated alkyl, a hydroxyl, an alkoxy, an aryloxy, an aralkoxy, an alkyl carboxylate, an unsaturated alkyl carboxylate, an aryl carboxylate, an amide, a sulfhydryl, an alkyl sulfide, an aryl sulfide, an alkyl sulfoxide, an aryl sulfoxide, an alkyl sulfonyl, an aryl sulfonyl, an alkylcarbonyl, an unsaturated alkyl carbonyl, an aryl carbonyl, an alkyl thiocarbonyl, an unsaturated alkyl thiocarbonyl, an aryl thiocarbonyl, a cyano, and a nitro;
any of the aryl-containing groups for $R^1$, $R^{1a}$, $R^2$, $R^{2a}$, $R^3$, $R^{3a}$, $R^4$ or $R^{4a}$ is unsubstituted or substituted with one or more substituents, which are the same or different, and selected from the group consisting of a halogen, a saturated alkyl, an unsaturated alkyl, a hydroxyl, an alkoxy, an aryloxy, an aralkoxy, an alkyl carboxylate, an unsaturated alkyl carboxylate, an aryl carboxylate, an amide, a sulfhydryl, an alkyl sulfide, an aryl sulfide, an alkyl sulfoxide, an aryl sulfoxide, an alkylsulfonyl, an arylsulfonyl, an alkylcarbonyl, an unsaturated alkyl carbonyl, an aryl carbonyl, an alkyl thiocarbonyl, an unsaturated alkyl thiocarbonyl, an aryl thiocarbonyl, a cyano, a nitro, an amino, an alkylamino and a dialkylamino; and
optionally, $R^1$ or $R^{1a}$ is attached to a solid support;
a, b, c, d, e and f are the same or different and each is H, a halogen, a saturated alkyl, an unsaturated alkyl, a hydroxyl, an alkoxy, an aryloxy, an aralkoxy, a cyano, a nitro, a sulfhydryl, an alkyl sulfide, an aryl sulfide, an alkyl sulfoxide, an aryl sulfoxide, an alkylsulfonyl, an arylsulfonyl, an alkylcarbonyl, an unsaturated alkyl carbonyl, an aryl carbonyl, an alkyl thiocarbonyl, an unsaturated alkyl thiocarbonyl, an aryl thiocarbonyl, an alkyl carboxylate, an unsaturated alkyl carboxylate, an aryl carboxylate, an amide, an amino, an alkylamino or a dialkylamino; and
R is a nucleosidyl group, an oligonucleotidyl group with 2 to about 300 nucleosides, or an oligomer with 2 to about 300 nucleosides;

n is an integer from 1 to about 300;
Lg is a leaving group;
$R^{5a}$ is a protecting group;
$R^{6a}$ is a protecting group or a solid support;
Q and $Q^1$ are the same or different and each is a linking substituent selected from the group consisting of nucleosidyl group, an oligonucleotidyl group with 2 to about 300 nucleosides, and an oligomer with 2 to about 300 nucleosides;
X is O, S or Se; and,
when n is greater than 1, each Q is independently selected.

13. The method of claim 12, wherein Z is $NR^2$.
14. The method of claim 12, wherein $R^2$ is H or a saturated alkyl.
15. The method of claim 12, wherein Y is $R^1$, and $R^1$ is a saturated alkyl or aryl.
16. The method of claim 12, wherein $R^3$ and $R^{3a}$ are H.
17. The method of claim 12, wherein $R^4$ and $R^{4a}$ are H, or one of $R^4$ and $R^{4a}$ are H and the other is aryl.
18. The method of claim 12, wherein Pg is selected from the group consisting of:

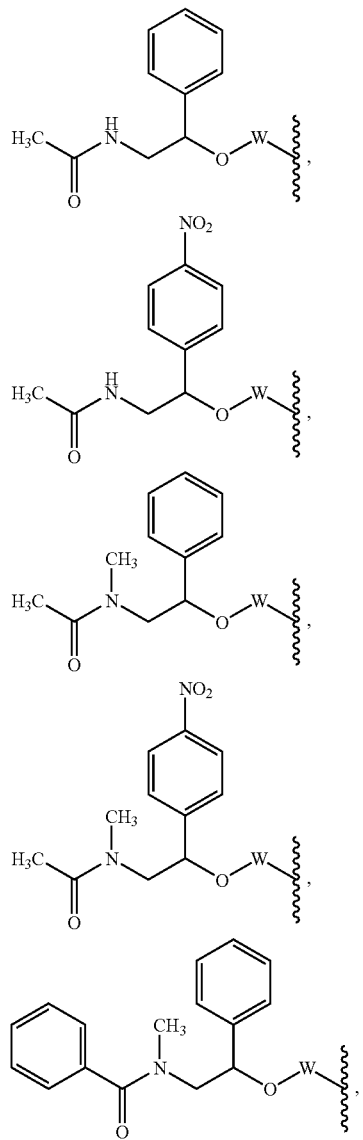

-continued

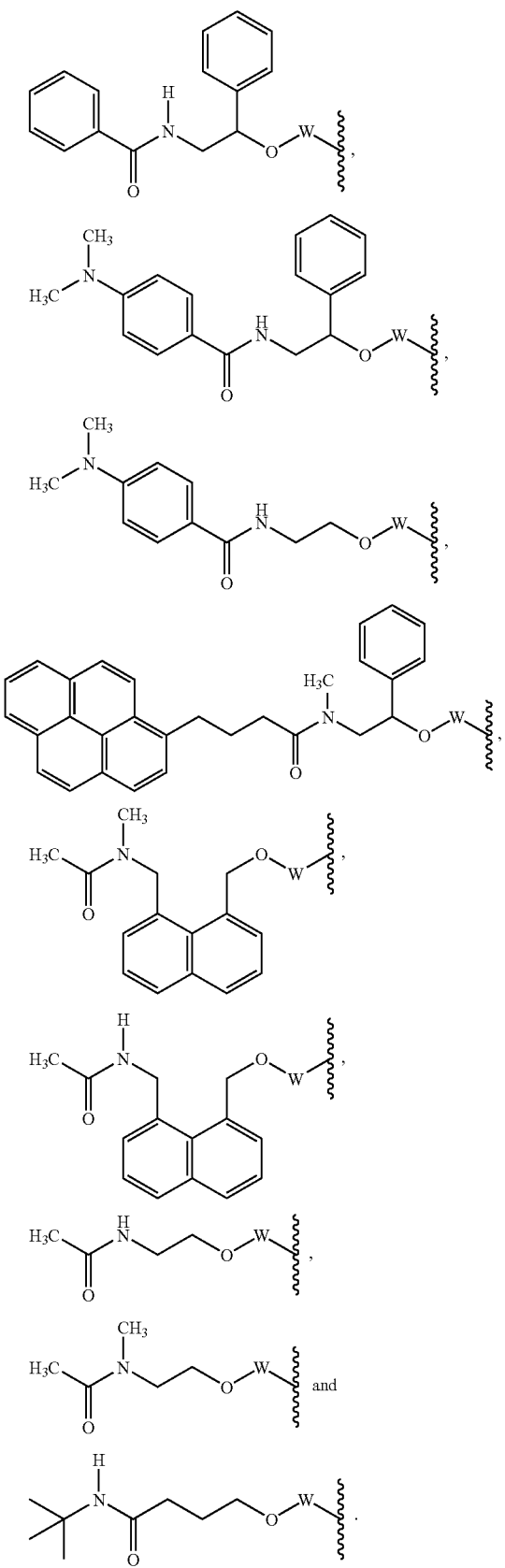

19. The method of claim 12, wherein R is of the formula:

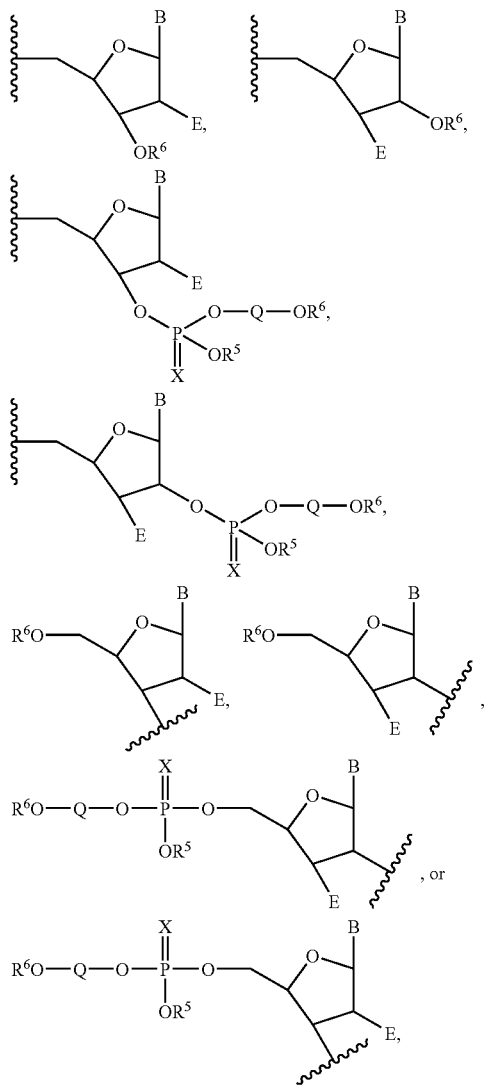

wherein:
Q is a linking substituent selected from the group consisting of nucleosidyl group, an oligonucleotidyl group with 2 to about 300 nucleosides, and an oligomer with 2 to about 300 nucleosides;

X is O, S or Se;

$R^5$ is H or a protecting group;

$R^6$ is H, a protecting group or a solid support;

B is a labeling group, a saturated alkyl, an unsaturated alkyl, a cycloalkyl, an aryl, a heteroaryl with 5 to about 10 atoms, including at least one heteroatom selected from the group consisting of O, N, S, an oxide of N, and an oxide of S in the ring skeleton thereof, a heterocloalkyl with 3 to about 10 atoms, including at least one heteroatom selected from the group consisting of O, N, S, an oxide of N, and an oxide of S in the ring skeleton thereof, a saturated alkyl with an aryl substituent, an unsaturated alkyl with an aryl substituent, an amino, an alkylamino, a dialkylamino, a purinyl, a pyrimidinyl, adeninyl, guaninyl, cytosinyl, uracilyl, or thyminyl, wherein B is unsubstituted or substituted with one or more substituents, which are the same or different, selected from the group consisting of a nucleobase protecting group, $R^7$, $OR^7$, $NHR^7$, $NR^7R^8$, $N{=}CH{-}NR^{7a}R^{8a}$, $N{=}C(alkyl)\text{-}NR^{7a}R^{8a}$, CN, $NO_2$, $N_3$, and a halogen, wherein $R^7$ and $R^8$ are the same or different and each is H, a saturated alkyl, an unsaturated alkyl, an alkylcarbonyl, an unsaturated alkyl carbonyl, an aryl carbonyl, an alkyl thiocarbonyl, an unsaturated alkyl thiocarbonyl, or an aryl thiocarbonyl, and $R^{7a}$ and $R^{8a}$ are the same or different and each is a saturated alkyl or an unsaturated alkyl, or, $R^{7a}$ and $R^{8a}$, together with the nitrogen atom to which they are bonded, form a heterocycle containing 3 to about 7 atoms in the ring skeleton thereof, and E is H, a halogen, $OR^9$, $NHR^9$, or $NR^9R^{10}$, wherein $R^9$ and $R^{10}$ are the same or different and each is H, a protecting group, a saturated alkyl, an unsaturated alkyl, an alkylcarbonyl, an unsaturated alkyl carbonyl, an aryl carbonyl, an alkyl thiocarbonyl, an unsaturated alkyl thiocarbonyl, or an aryl thiocarbonyl.

20. The method of claim 12, wherein R is of the formula:

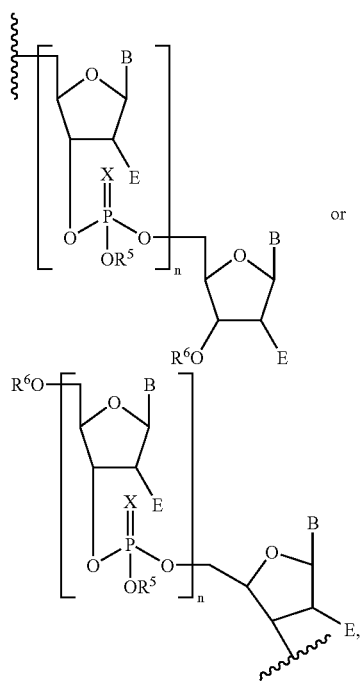

wherein
n is an integer from 0 to about 300

X is O, S or Se;

$R^5$ is H or a protecting group;

$R^6$ is H, a protecting group or a solid support;

B is a labeling group, a saturated alkyl, an unsaturated alkyl, a cycloalkyl, an aryl, a heteroaryl with 5 to about 10 atoms, including at least one heteroatom selected from the group consisting of O, N, S, an oxide of N, and an oxide of S in the ring skeleton thereof, a heterocloalkyl with 3 to about 10 atoms, including at least one heteroatom selected from the group consisting of O, N, S, an oxide of N, and an oxide of S in the ring skeleton thereof, a saturated alkyl with an aryl substituent, an unsaturated alkyl with an aryl substituent, an amino, an alkylamino, a dialkylamino, a purinyl, a pyrimidinyl, adeninyl, guaninyl, cytosinyl, uracilyl, or thyminyl, wherein B is unsubstituted or substituted with one or more substituents, which are the same or different, selected from the group consisting of a nucleobase protecting group, $R^7$, $OR^7$, $NHR^7$, $NR^7R^8$, $N=CH-NR^{7a}R^{8a}$, $N=C(alkyl)-NR^{7a}R^{8a}$a, CN, $NO_2$, $N_3$, and a halogen, wherein $R^7$ and $R^8$ are the same or different and each is H, a saturated alkyl, an unsaturated alkyl, an alkylcarbonyl, an unsaturated alkyl carbonyl, an aryl carbonyl, an alkyl thiocarbonyl, an unsaturated alkyl thiocarbonyl, or an aryl thiocarbonyl, and $R^{7a}$ and $R^{8a}$ are the same or different and each is a saturated alkyl or an unsaturated alkyl, or, $R^{7a}$ and $R^{8a}$, together with the nitrogen atom to which they are bonded, form a heterocycle containing 3 to about 7 atoms in the ring skeleton thereof, and E is H, a halogen, $OR^9$, $NHR^9$, or $NR^9R^{10}$, wherein $R^9$ and $R^{10}$ are the same or different and each is H, a protecting group, a saturated alkyl, an unsaturated alkyl, an alkylcarbonyl, an unsaturated alkyl carbonyl, an aryl carbonyl, an alkyl thiocarbonyl, an unsaturated alkyl thiocarbonyl, or an aryl thiocarbonyl.

21. The method of claim 19, wherein B is selected from the group consisting of a purinyl, a pyrimidinyl, adeninyl, guaninyl, cytosinyl, uracilyl, and thyminyl.

22. The method of claim 20, wherein B is selected from the group consisting of a purinyl, a pyrimidinyl, adeninyl, guaninyl, cytosinyl, uracilyl, and thyminyl.

23. The method of claim 21, wherein B is selected from the group consisting of unsubstituted adeninyl, unsubstituted or substituted guaninyl, unsubstituted or substituted cytosinyl, and unsubstituted or substituted thyminyl.

24. The method of claim 22, wherein B is selected from the group consisting of unsubstituted adeninyl, unsubstituted or substituted guaninyl, unsubstituted or substituted cytosinyl, and unsubstituted or substituted thyminyl.

25. The hydroxyl-protected alcohol of claim 10, wherein B is selected from the group consisting of unsubstituted adeninyl, unsubstituted or substituted guaninyl, unsubstituted or substituted cytosinyl, and unsubstituted or substituted thyminyl.

26. The process of claim 12 further comprising wherein, in step (f) of said process, the oligonucleotidyl group, the polynucleotidyl group, or the nucleoside-containing oligomeric group is cleaved from the solid support $R^{6a}$.

* * * * *